United States Patent
Hanashi et al.

(10) Patent No.: US 8,958,066 B2
(45) Date of Patent: *Feb. 17, 2015

(54) OPTICAL ANALYSIS METHOD USING MEASUREMENT OF LIGHT OF TWO OR MORE WAVELENGTH BANDS

(71) Applicant: Olympus Corporation, Tokyo (JP)

(72) Inventors: Takuya Hanashi, Hachioji (JP); Tetsuya Tanabe, Tokyo (JP); Mitsushiro Yamaguchi, Hachioji (JP); Hidetaka Nakata, Hachijoji (JP)

(73) Assignee: Olympus Corporation, Tokyo (JP)

( * ) Notice: Subject to any disclaimer, the term of this patent is extended or adjusted under 35 U.S.C. 154(b) by 62 days.

This patent is subject to a terminal disclaimer.

(21) Appl. No.: 13/789,111

(22) Filed: Mar. 7, 2013

(65) Prior Publication Data

US 2013/0230874 A1 Sep. 5, 2013

Related U.S. Application Data

(63) Continuation of application No. PCT/JP2011/069440, filed on Aug. 29, 2011.

(30) Foreign Application Priority Data

Sep. 10, 2010 (JP) ................. 2010-202994

(51) Int. Cl.
*G01N 21/00* (2006.01)
*G01N 21/64* (2006.01)
(52) U.S. Cl.
CPC ........ *G01N 21/6486* (2013.01); *G01N 21/6452* (2013.01); *G01N 21/6458* (2013.01); *G01N 21/6428* (2013.01)
USPC ............................ 356/337; 356/341; 356/343

(58) Field of Classification Search
USPC .................................................. 356/335–344
See application file for complete search history.

(56) References Cited

U.S. PATENT DOCUMENTS

| 4,251,733 A | 2/1981 | Hirleman, Jr. |
| 5,866,336 A | 2/1999 | Nazarenko et al. |

(Continued)

FOREIGN PATENT DOCUMENTS

| EP | 1 906 172 A1 | 4/2008 |
| JP | 04-337446 A | 11/1992 |

(Continued)

OTHER PUBLICATIONS

Kinjo, Masataka, "Single molecule protein, nucleic acid, and enzyme assays and their procedures; Single molecule detection by fluorescence correlation spectroscopy", Protein, Nucleic Acid, Enzyme, 1999, vol. 44, No. 9, pp. 1431-1438, w/ English translation.

(Continued)

*Primary Examiner* — Tarifur Chowdhury
*Assistant Examiner* — Jarreas C Underwood
(74) *Attorney, Agent, or Firm* — Westerman, Hattori, Daniels & Adrian, LLP

(57) ABSTRACT

There is provided an optical analysis technique enabling identification of a kind of light-emitting particle corresponding to a signal on a time series light intensity data or identification of a signal corresponding to light-emitting particles other than a particle to be observed in an optical measurement using a confocal microscope or a multiphoton microscope. The inventive optical analysis technique measures simultaneously and separately intensities of lights of two or more wavelength bands from a light detection region in a sample solution containing light-emitting particles of two or more kinds to generate time series light intensity data of the respective wavelength bands; detects signals simultaneously generated on the time series light intensity data of at least two wavelength bands; and identifies the simultaneously generated signals as signals of a light-emitting particle of at least one specific kind.

15 Claims, 12 Drawing Sheets

(56) References Cited

U.S. PATENT DOCUMENTS

Figures 1A, 1B, 1C:
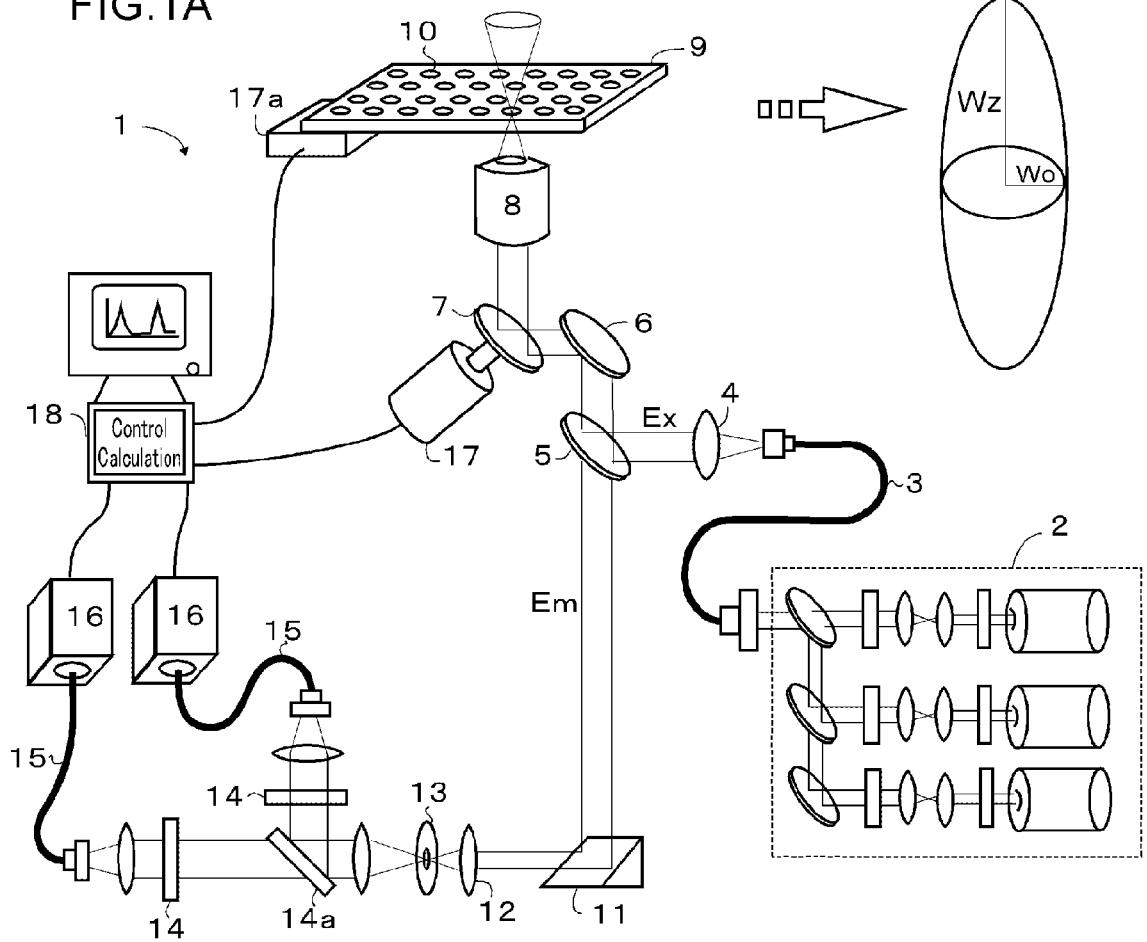

| | | |
|---|---|---|
| 6,280,960 B1 | 8/2001 | Carr |
| 6,376,843 B1 | 4/2002 | Palo |
| 6,388,746 B1 | 5/2002 | Eriksson et al. |
| 6,388,788 B1 * | 5/2002 | Harris et al. .............. 359/196.1 |
| 6,400,487 B1 | 6/2002 | Harris et al. |
| 6,403,338 B1 | 6/2002 | Knapp et al. |
| 6,586,193 B2 * | 7/2003 | Yguerabide et al. .............. 506/3 |
| 6,710,871 B1 | 3/2004 | Goix |
| 6,856,391 B2 | 2/2005 | Garab et al. |
| 6,927,401 B1 | 8/2005 | Palo |
| 7,551,763 B2 * | 6/2009 | Calvin et al. .................. 382/133 |
| 8,284,484 B2 | 10/2012 | Hoult et al. |
| 8,711,353 B2 * | 4/2014 | Kaye et al. ..................... 356/342 |
| 8,804,119 B2 * | 8/2014 | Knox et al. .................... 356/337 |
| 2001/0035954 A1 | 11/2001 | Rahn et al. |
| 2002/0008211 A1 | 1/2002 | Kask |
| 2002/0036775 A1 | 3/2002 | Wolleschensky et al. |
| 2003/0036855 A1 | 2/2003 | Harris et al. |
| 2003/0218746 A1 * | 11/2003 | Sampas ........................ 356/318 |
| 2004/0022684 A1 | 2/2004 | Heinze et al. |
| 2004/0051051 A1 * | 3/2004 | Kato et al. ................. 250/458.1 |
| 2004/0150880 A1 | 8/2004 | Nakata et al. |
| 2004/0219535 A1 | 11/2004 | Bell et al. |
| 2005/0179892 A1 | 8/2005 | Gerstner et al. |
| 2005/0213090 A1 * | 9/2005 | Namba et al. ................. 356/318 |
| 2005/0260660 A1 | 11/2005 | Van Dongen et al. |
| 2006/0078998 A1 | 4/2006 | Puskas et al. |
| 2006/0158721 A1 | 7/2006 | Nakata et al. |
| 2006/0256338 A1 | 11/2006 | Gratton et al. |
| 2008/0052009 A1 | 2/2008 | Chiu et al. |
| 2008/0117421 A1 | 5/2008 | Yamaguchi et al. |
| 2008/0268548 A1 * | 10/2008 | Zuckerman .................. 436/172 |
| 2009/0159812 A1 | 6/2009 | Livingston |
| 2009/0230324 A1 | 9/2009 | Gratton et al. |
| 2010/0033718 A1 | 2/2010 | Tanaami |
| 2010/0177190 A1 | 7/2010 | Chiang et al. |
| 2010/0202043 A1 | 8/2010 | Ujike |
| 2011/0204258 A1 | 8/2011 | Heller et al. |

FOREIGN PATENT DOCUMENTS

| | | |
|---|---|---|
| JP | 2002-022640 A | 1/2002 |
| JP | 2002-507762 A | 3/2002 |
| JP | 2002-525579 A | 8/2002 |
| JP | 2002-543414 A | 12/2002 |
| JP | 2003-522969 A | 7/2003 |
| JP | 2004-506192 A | 2/2004 |
| JP | 3517241 B2 | 4/2004 |
| JP | 2004-251814 A | 9/2004 |
| JP | 2005-098876 A | 4/2005 |
| JP | 2005-099662 A | 4/2005 |
| JP | 2005-509857 A | 4/2005 |
| JP | 2005-524051 A | 8/2005 |
| JP | 2006-525517 A | 11/2006 |
| JP | 2007-020565 A | 2/2007 |
| JP | 4023523 B2 | 12/2007 |
| JP | 2008-116440 A | 5/2008 |
| JP | 2008-536093 A | 9/2008 |
| JP | 2008-538609 A | 10/2008 |
| JP | 2008-292371 A | 12/2008 |
| JP | 2009-145242 A | 7/2009 |
| JP | 2009-281831 A | 12/2009 |
| JP | 2009-288161 A | 12/2009 |
| JP | 2010-190730 A | 9/2010 |
| JP | 2011-002415 A | 1/2011 |
| WO | 94/16313 A2 | 7/1994 |
| WO | 98/16814 A1 | 4/1998 |
| WO | 99/47963 A1 | 9/1999 |
| WO | 00/66985 A1 | 11/2000 |
| WO | 02/12864 A1 | 2/2002 |
| WO | 2006/084283 A2 | 8/2006 |
| WO | 2007/010803 A1 | 1/2007 |
| WO | 2007/147159 A2 | 12/2007 |
| WO | 2008/007580 A1 | 1/2008 |
| WO | 2008/080417 A1 | 7/2008 |
| WO | 2009/117033 A2 | 9/2009 |
| WO | 2010/084719 A1 | 7/2010 |
| WO | 2011/108369 A1 | 9/2011 |
| WO | 2011/108371 A1 | 9/2011 |

OTHER PUBLICATIONS

Meyer-Almes, F.J., "Nanoparticle Immunoassays: A new Method for Use in Molecular Diagnostics and High Throughput Pharmaceutical Screening based on Fluorescence Correlation Spectroscopy", edit. R. Rigler, Springer, Berlin, 2000, pp. 204-224.

Schwille, Petra, et al., "Dual-Color Fluorescence Cross-Correlation Spectroscopy for Multicomponent Diffusional Analysis in Solution", Biophysical Journal, 1997, vol. 72, pp. 1878-1886.

International Search Report of PCT/JP2011/069440, mailing date of Nov. 29, 2011.

International Search Report dated Dec. 13, 2011, issued in related PCT/JP2011/069738.

International Search Report dated Mar. 29, 2011, issued in related PCT/JP2011/053481.

Park, Mira et al., "Counting the Number of Fluorophores Labeled in Biomolecules by Observing the Fluorescence-Intensity Transient of a Single Molecule", Bulletin of the Chemical Society of Japan, dated Aug. 30, 2005, vol. 78, No. 9, (p. 1612-1618).

Kask, Peet et al., "Two-Dimensional Fluorescence Intensity Distribution Analysis: Theory and Applications", Biophysical Journal, Apr. 2000, vol. 78, (p. 1703-1713).

Carlsson, K. et al., "Three-dimensional Microscopy Using a Confocal Laser Scanning Microscope", Optics Letters, Optical Society of America, Feb. 1985, vol. 10, No. 2, p. 53-55, XP007922413.

Chinese Office Action dated Aug. 13, 2013, issued in related Chinese application No. 201180011655.3; w/ English Translation (16 pages).

International Search Report dated Mar. 29, 2011, issued in related PCT/JP2011/053483.

International Preliminary Report on Patentability (PCT/IPEA/409) issued in related PCT/JP2011/053483.

Chinese Office Action dated Aug. 9, 2013, issued in related Chinese application No. 201180011640.7; w/ English Translation (16 pages).

International Search Report Mar. 29, 2011, issued in related PCT/JP2011/053482.

International Preliminary Report on Patentability (PCT/IPEA/409) issued in related PCT/JP2011/053482.

U.S. Office Action dated Jan. 3, 2013, issued in related U.S. Appl. No. 13/597,825.

Chinese Office Action dated Feb. 7, 2013, issued in related Chinese application No. 201180011644.5; w/ English Translation (18 pages).

Japanese Office Action dated Dec. 18, 2012 issued in related JP application No. 2012-503060; w/ English Translation (6 pages).

International Preliminary Report on Patentability (PCT/IPEA/409) issued in related PCT/JP2011/053481.

Goodwin, Peter et al., "Rapid Sizing of Individual Fluorescently Stained DNA Fragments by Flow Cytometry," Nucleic Acids Research, 1993, vol. 21, No. 4 (p. 803-806).

Keller, Richard et al., "Single-Molecule Fluorescence Analysis in Solution," Applied Spectroscopy, 1996, vol. 50, No. 7, (p. 12A-32A).

Lee, Yuan-Hsiang et al., "Laser-Induced Fluorescence Detection of a Single Molecule in a Capillary," Analytical Chemistry, dated Dec. 1, 1994, vol. 66, No. 23, (p. 4142-4149).

Li, Haitao et al., "Ultrasensitive Conincidence Fluorescence Detection of Single DNA Molecules," Analytical Chemistry, dated Apr. 1, 2003, vol. 75, No. 7, (p. 1664-1670).

Nie, Shuming et al., "Probing Individual Molecules with Confocal Fluorescence Microscopy," Science, dated Nov. 11, 1994, vol. 266, (p. 1018-1021).

Tahari, Abdel. "Fluorescence Correlation Spectroscopy: Ultrasensitive Detection in Clear and Turbid Media," University of Illinois, 2006, (p. 1-88).

Wu, Alan et al., "Development and Preliminary Clinical Validation of a High Sensitivity Assay for Cardiac Troponin Using a Capillary Flow (Single Molecule) Fluorescence Detector," Clinical Chemistry, 2006, vol. 52, No. 11, (p. 2157-2159).

(56) References Cited

OTHER PUBLICATIONS

U.S. Office Action dated Oct. 4, 2013, issued in related U.S. Appl. No. 13/596,243.
International Search Report dated Feb. 14, 2012, issued in related PCT/JP2011/076151.
Kask, Peet et al., "Fluorescence-intensity Distribution Analysis and its Application in Biomolecular Detection Technology", PNAS, dated Nov. 23, 1999, vol. 96, No. 24, (p. 13756-13761).
U.S. Office Action dated Nov. 29, 2013, issued in co-pending U.S. Appl. No. 13/788,972.
U.S. Office Action dated Apr. 2, 2013, issued in related U.S. Appl. No. 13/596,280.
European Search Report dated Oct. 24, 2013, issued in related EP application No. 11823457.4.
European Search Report dated Dec. 20, 2013, issued in related EP application No. 11843762.3.
Extended European Search Report dated Mar. 28, 2013, issued in related EP application No. 11750481.1.
International Search Report Nov. 29, 2011, issued in related PCT/JP2011/072939.
Official Notice of Jul. 28, 2014 issued in related application EP 11823457.4 (4 pages).
European Official Communication dated Jul. 14, 2014, issued in related European Patent Application No. 11843762.3 (10 pages).
Chinese Office Action dated Jun. 27, 2014, issued in related Chinese Patent Application No. 201180043161.3 with English translation (14 pages).
Chinese Office Action dated Jul. 30, 2014, issued in related Chinese Patent Application No. 201180057025.X with English translation (17 pages).
Office Action dated Sep. 26, 2014, issued in related Chinese Patent Application No. 201180043734.2, with English Translation (10 pages).
Communication pursuant to Article 94(3) EPC dated Nov. 24, 2014, issued in related European Patent Application No. 11843762.3 (7 pages).

\* cited by examiner

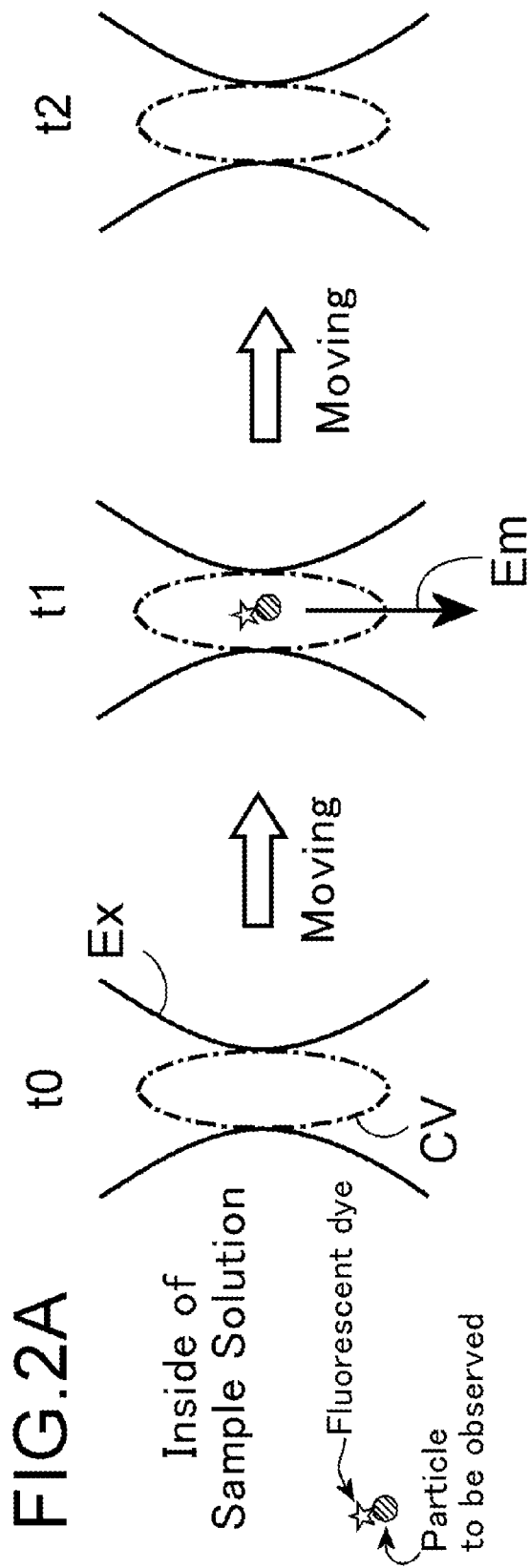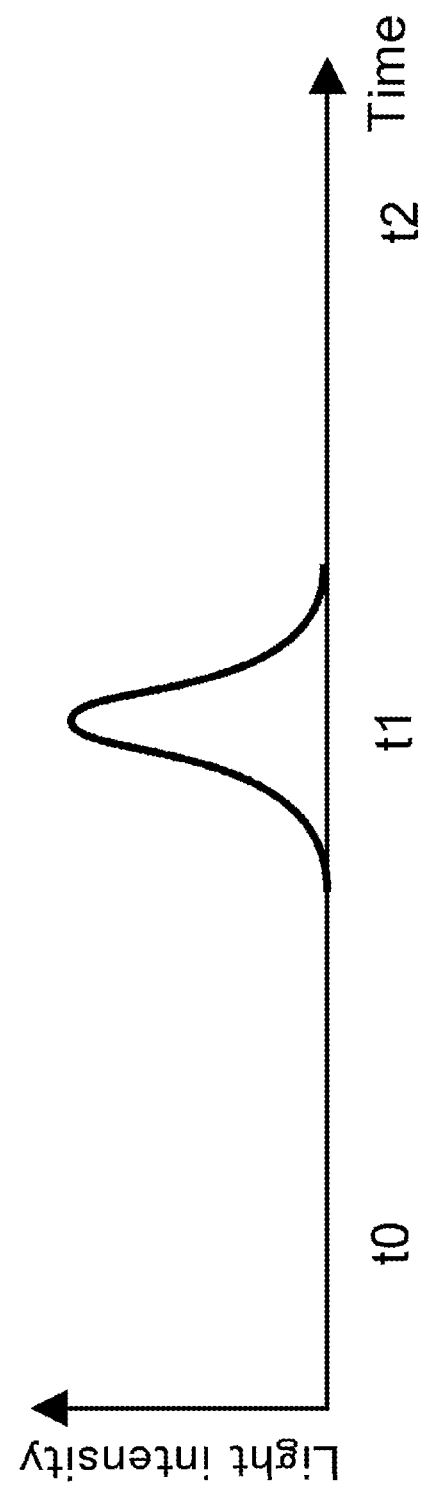

FIG.5A
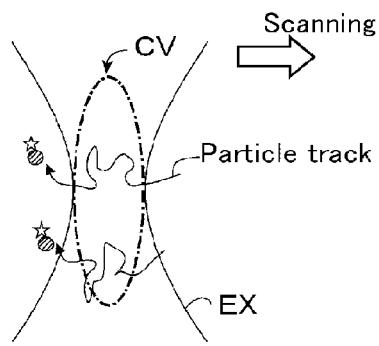
FIG.5B
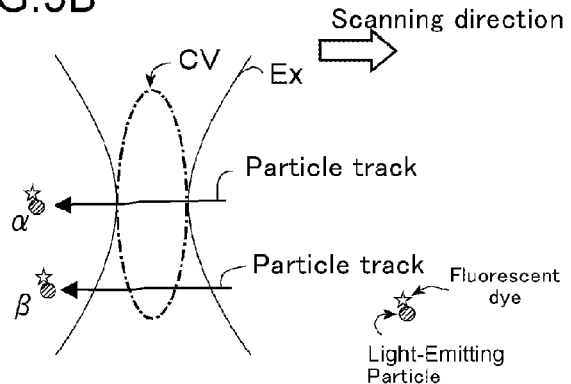
FIG.5C
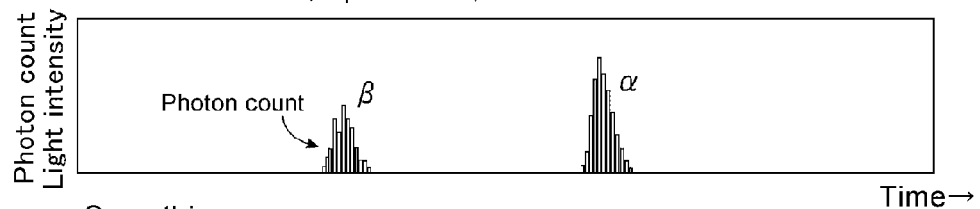
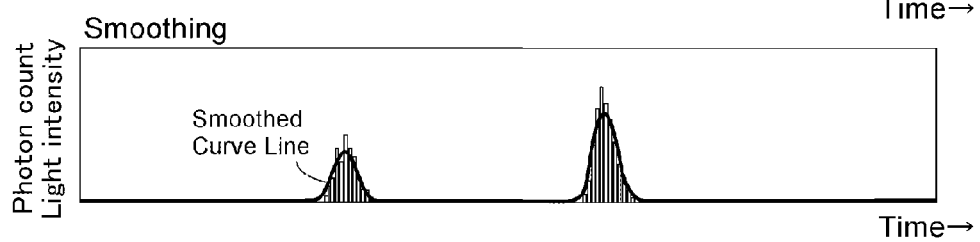
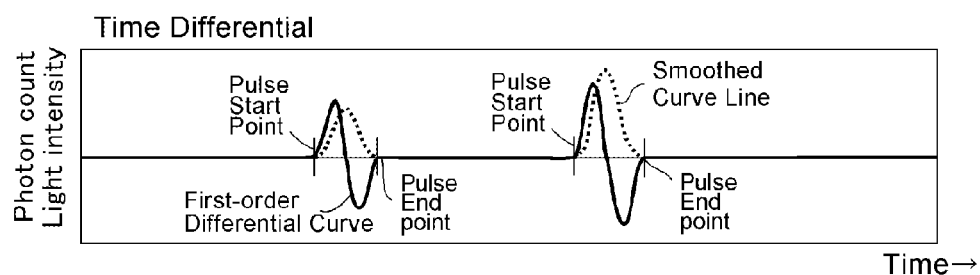
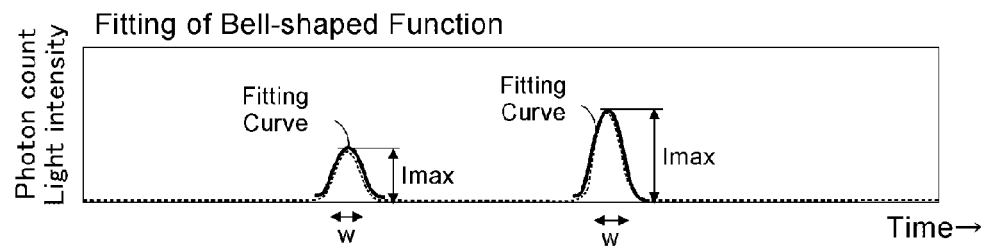

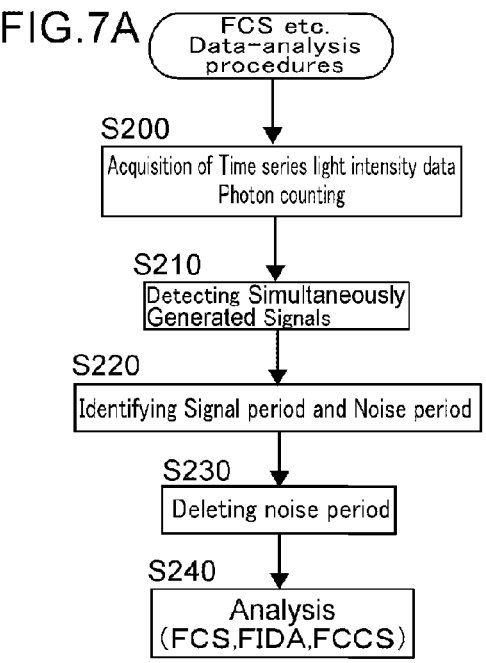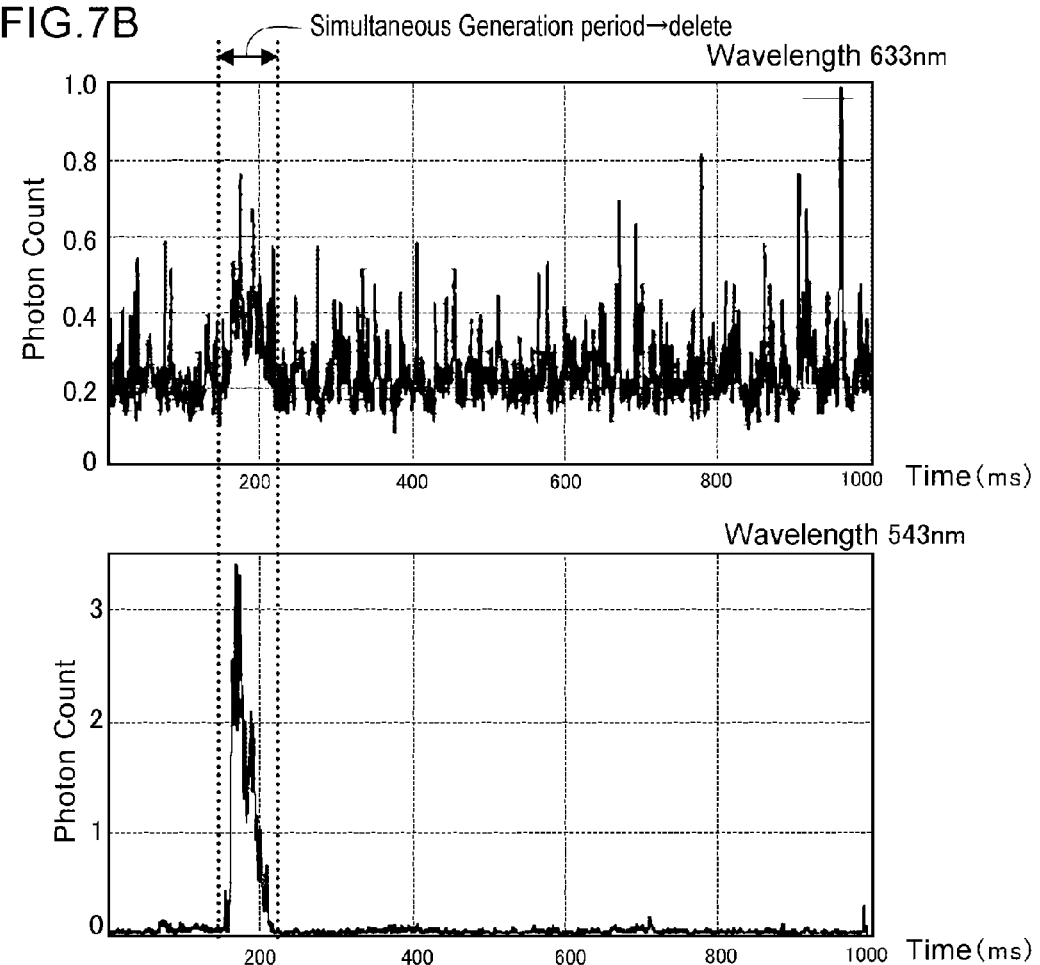

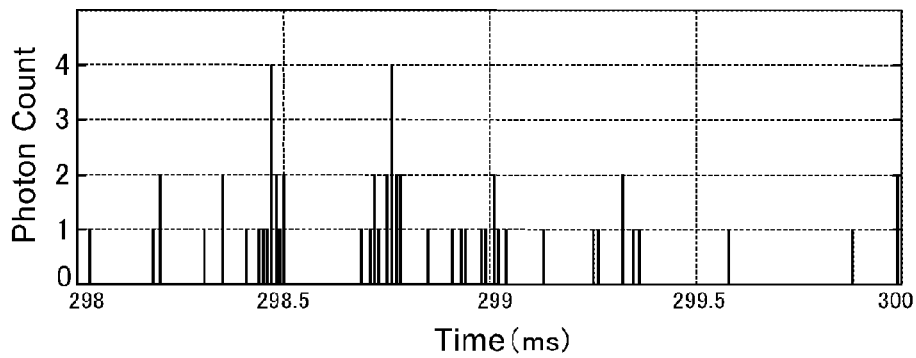
FIG.8A Photon count data (excitation wavelength of 488 nm)
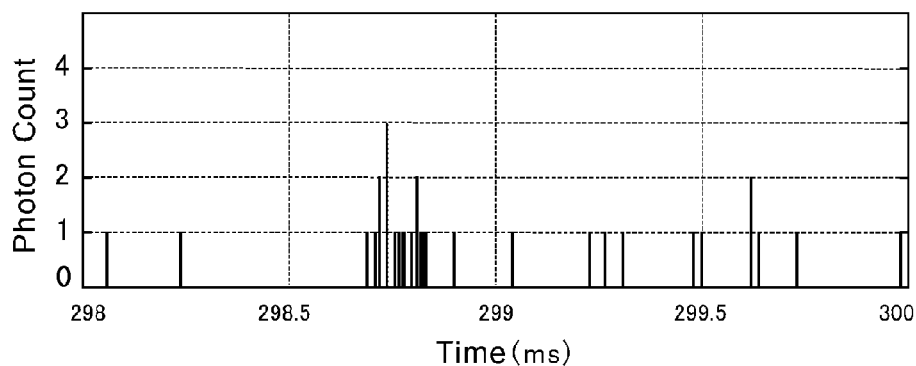
FIG.8B Photon count data (excitation wavelength of 633 nm)
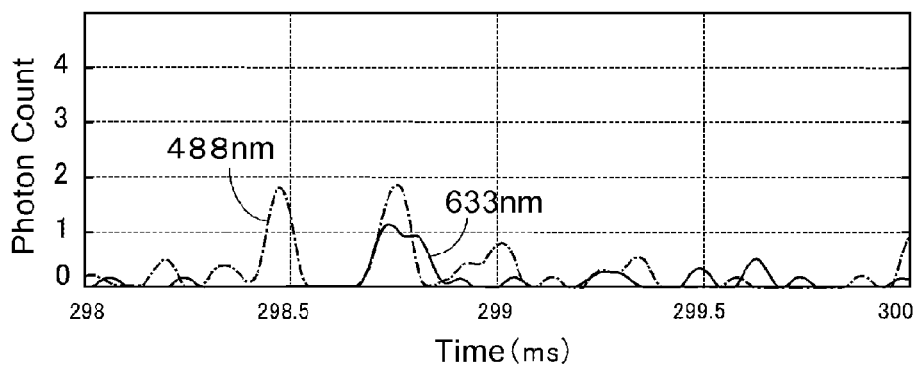
FIG.8C Smoothed data
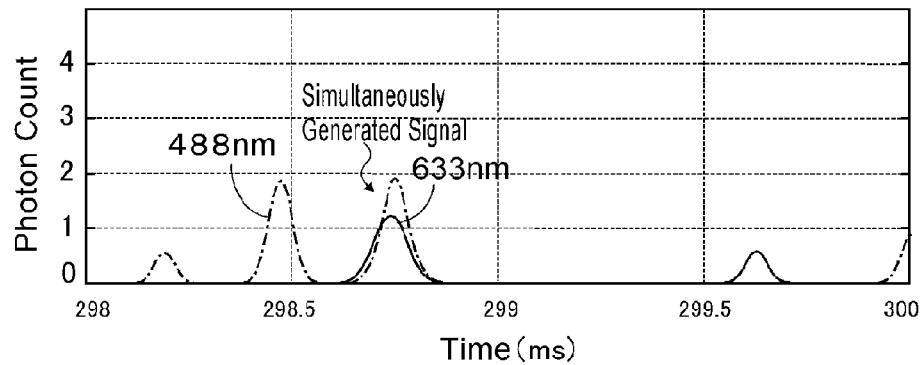
FIG.8D Fitting data

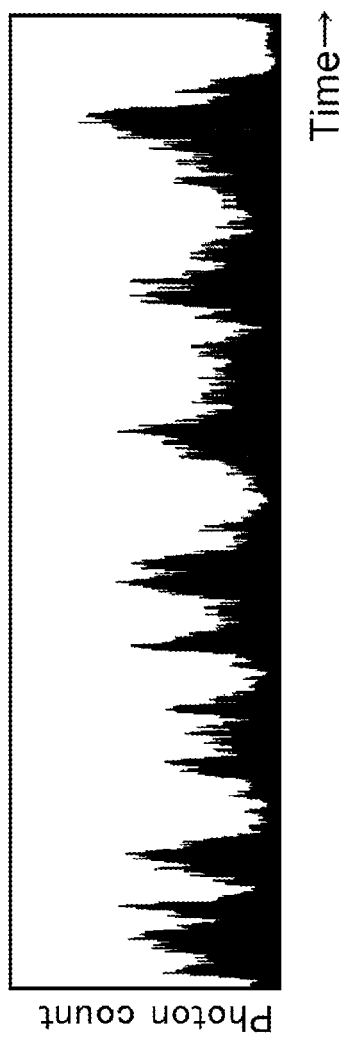
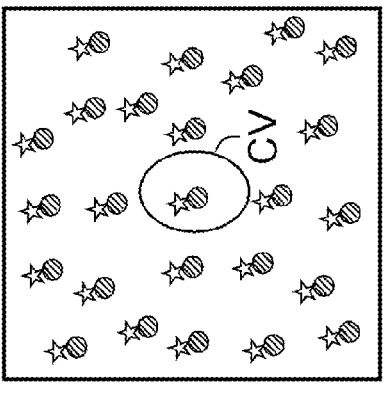
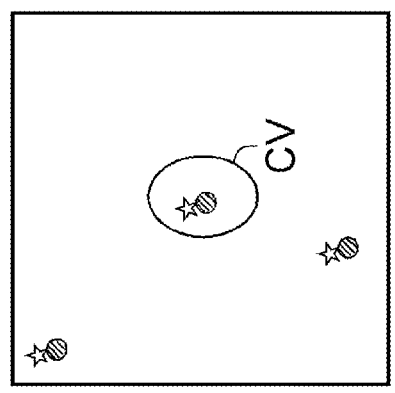
FIG.12A High Concentration (e. g. ~ 1nM)
FIG.12B Low Concentration (e. g. ~ 1pM)

OPTICAL ANALYSIS METHOD USING MEASUREMENT OF LIGHT OF TWO OR MORE WAVELENGTH BANDS

TECHNICAL FIELD

This invention relates to an optical analysis method capable of detecting light from a particulate object, e.g. an atom, a molecule or an aggregate thereof (Hereafter, these are called a "particle".), such as a biological molecule, for example, protein, peptide, nucleic acid, lipid, sugar chain, amino acid or these aggregate, virus and cell, etc., or a non-biological particle, dispersed or dissolved in a solution, by using an optical system, such as the optical system of a confocal microscope or a multiphoton microscope, which can detect light from a micro region in a solution, to acquire useful information in an analysis of conditions (interaction, binding or dissociating condition, etc.) of particles, and more specifically, relates to a method of performing a measurement of lights of two or more wavelength bands using an optical system as described above, to make it possible to conduct various optical analyses, in which a kind of particle is identified, or where a signal from a particle wanted to observe (particle to be observed) is distinguished from other signals or noise in the measurement result. In this regard, in this specification, a particle which emit light (hereafter, referred to as a "light-emitting particle") may be either of a particle which itself emits light and a particle to which an arbitrary light-emitting label has been attached, and the light emitted from a light-emitting particle may be fluorescence, phosphorescence, chemiluminescence, bioluminescence, scattered light, etc.

BACKGROUND ART

According to the developments in optical measurement techniques in recent years, detection and/or measurement of faint light at a single photon or single fluorescent molecule level have become possible by using an optical system of a confocal microscope and a super high sensitive light detection technique capable of the photon counting (single photon detection). Thus, there are variously proposed devices or methods of performing detection of a characteristic, an intermolecular interaction, a binding or dissociating reaction of a biological molecule, etc. by means of such a faint light measurement technique. For example, in Fluorescence Correlation Spectroscopy (FCS, see e.g. patent documents 1 and 2 and non-patent documents 1-3), by means of the optical system of a laser confocal microscope and a photon counting technique, there is performed the measurement of fluorescence intensity of fluorescent molecules or fluorescently labeled molecules (fluorescent molecules, etc.), entering into and exiting out of a micro region in a sample solution (the focal region to which the laser light of the microscope is condensed, called a "confocal volume"), and based on the average dwell time (translational diffusion time) of the fluorescent molecules, etc. and the average value of the number of the dwelling molecules in the micro region, determined from the autocorrelation function value of the measured fluorescence intensity, there are achieved the acquisition of information, such as the motion speed, the size or the concentration of the fluorescent molecules, etc., and/or the detection of various phenomena, such as a change of a molecular structure or size, a binding or dissociative reaction or dispersion and aggregation of molecules. Further, in Fluorescence cross-correlation Spectroscopy (FCCS, e.g. nonpatent document 4 and patent documents 5), for a sample solution containing fluorescent molecules, etc. having two different emission wavelengths, the light intensities of two emission wavelengths are measured using the same device as FCS, and based on the value of the cross correlation function of the measured light intensities of the two emission wavelengths, there is estimated whether or not a correlation exists in the motions of two particles emitting fluorescences of different emission wavelengths, namely whether or not those particles mutually associate or interact, or the number or ratio of interacting substances. Moreover, in Fluorescence Intensity Distribution Analysis (FIDA, e.g. patent document 3) or Photon Counting Histogram (PCH, e.g. patent document 4), there is generated a histogram of fluorescence intensity of fluorescent molecules, etc., entering into and exiting out of a confocal volume, measured similarly to FCS; and the average value of the characteristic brightness of the fluorescent molecules, etc. and the average number of molecules dwelling in the confocal volume are calculated by fitting a statistical model formula to the distribution of the histogram, so that, based on the information thereof, the structure or size changes, binding or dissociative conditions or dispersion and aggregation conditions of molecules can be estimated. In addition, in patent documents 6 and 7, there are proposed methods of detecting fluorescent substances based on a time progress of fluorescence signals of a sample solution measured using the optical system of a confocal microscope. Patent document 8 has proposed a signal calculation processing technique for measuring faint light from fluorescent fine particles flowing through a flow cytometer or fluorescent fine particles fixed on a substrate by a photon counting technique to detect the existences of the fluorescent fine particles in the flow or on the substrate.

Especially, according to the methods employing the measurement technique of fluorescent light of a micro region using the optical system of a confocal microscope and a photon counting technique, such as FCS, FCCS and FIDA, a sample amount required for the measurement may be extremely small (an amount used in one measurement is at most several tens of $\mu$L), and its concentration is extremely low as compared with the prior art, and the measuring time is also shortened extremely (In one measurement, a measuring process for time of order of seconds is repeated several times.). Thus, those techniques are expected to be a strong tool enabling an experiment or a test at low cost and/or quickly in comparison with conventional biochemical methods, especially in conducting an analysis of a rare or expensive sample often used in the field of the medical or biological research and development or in conducting tests of a large number of specimens, such as sick clinical diagnosis or the screening of bioactive substances.

PRIOR TECHNICAL DOCUMENTS

Patent Documents

Patent document 1: Japanese Patent laid-open publication No. 2005-098876
Patent document 2: Japanese Patent laid-open publication No. 2008-292371
Patent document 3: Japanese Patent No. 4023523
Patent document 4: WO 2008-080417
Patent document 5: Japanese Patent No. 3517241
Patent document 6: Japanese Patent laid-open publication No. 2007-20565
Patent document 7: Japanese Patent laid-open publication No. 2008-116440
Patent document 8: Japanese Patent laid-open publication No. 4-337446

Non-Patent Documents

Non-patent document 1: Masataka Kaneshiro; "Protein, Nucleic acid, Enzyme" Vol. 44, No. 9, pages 1431-1438, 1999.
Non-patent document 2: F. J. Meyer-Alms; "Fluorescence Correlation Spectroscopy" edt. R. Rigler, Springer, Berlin, pages 204-224, 2000.
Non-patent document 3: Noriko Kato, et al. "Gene medicine", Vol. 6, No. 2, pages 271-277.
Non-patent document 4: Biophysical Journal, Volume 72 (1997) 1878-1886

SUMMARY OF INVENTION

Technical Problem

In the above-mentioned optical analysis technique using the optical system of a confocal microscope and a photon counting technique, such as FCS, FCCS, and FIDA, although the measured light is the light emitted from single or several fluorescent molecules, there are conducted in the analysis of the light the statistical procedures for calculating the fluorescence intensity fluctuation such as the computation of the autocorrelation function or cross correlation function or the fitting to the histogram of fluorescence intensity data measured in time series, and therefore the signal of the light from an individual fluorescent molecule is not seen or analyzed. That is, in these optical analysis techniques, through the statistical processing of the signals of the lights from a plurality of fluorescent molecules, etc., statistical average characteristics of the fluorescent molecules, etc. will be detected. Thus, in order to obtain a statistically significant result in these optical analysis techniques, the concentration or number density of a fluorescent molecule, etc. to be an observation object in the sample solution should be at a level so that fluorescent molecules, etc. of the number enabling a statistical process will enter in and exit from a micro region in one measuring term of a length of order of seconds in an equilibrium, preferably so that about one fluorescent molecule, etc. will be always present in the micro region. Actually, since the volume of a confocal volume is about 1 fL, the concentration of a fluorescent molecule, etc. in a sample solution used in the above-mentioned optical analysis technique is typically at the level of 1 nM or more, and at much less than 1 nM, there is produced a term in which no fluorescent molecules, etc. are present in the confocal volume so that no statistically significant analysis result will be obtained. On the other hand, in the detection methods of fluorescent molecules, etc. described in patent documents 6-8, no statistical computation processes of fluorescence intensity are included so that fluorescent molecules, etc. even at less than 1 nM in a sample solution can be detected, but, it has not been achieved to compute quantitatively the concentration or number density of a fluorescent molecule, etc. moving at random in a solution.

Then, in Japanese patent application No. 2010-044714 and PCT/JP2011/53481, Applicant of the present application has proposed an optical analysis technique based on a new principle which makes it possible to observe quantitatively a condition or characteristic of a light-emitting particle in a sample solution where the concentration or number density of the light-emitting particle to be an observation object is lower than the level at which the optical analysis techniques including statistical procedures, such as FCS, FCCS, and FIDA are used. In this new optical analysis technique, briefly, there is used an optical system which can detect light from a micro region in a solution, such as an optical system of a confocal microscope or a multiphoton microscope, similarly to FCS, FCCS, FIDA, etc., and additionally, the position of the micro region, i.e. a light detection region, is moved in the sample solution, namely, the inside of the sample solution is scanned with the micro region, and when a light-emitting particle, dispersed and moving at random in the sample solution, crosses the inside of the micro region, the light emitted from the light-emitting particle is detected, and thereby each of the light-emitting particles in the sample solution is detected individually so that it becomes possible to perform the counting of light-emitting particles and the acquisition of the information about the concentration or number density of the light-emitting particle in the sample solution. According to this new optical analysis technique (called a "scanning molecule counting method", hereafter.), not only a sample amount necessary for measurement may be small (for example, about several 10 μL) and the measuring time is short similarly to optical analysis techniques, such as FCS, FCCS and FIDA, but also, it becomes possible to detect the presence of a light-emitting particle and to quantitatively detect its characteristic, such as a concentration or a number density, at a lower concentration or number density, as compared with the cases of optical analysis techniques, such as FCS, FCCS and FIDA.

By the way, in the above-mentioned scanning molecule counting method, under the assumption that the light emitted by one light-emitting particle when it has entered into the light detection region appears as an intensity change having a crested or almost bell shaped profile i.e. a pulse form signal on a time series light intensity data, and each pulse form signal corresponds to each light-emitting particle, the pulse form signal is detected one by one on the time series light intensity data, and the number of the detected pulse form signals is counted as the number of the light-emitting particles which passed through the light detection region. However, in that case, light-emitting particles of mutually different kinds having the same emission wavelength are mutually undistinguishable, or, if there is a light-emitting particle which is different from a light-emitting particle to be an observation object and also has the same emission wavelength as the particle to be observed in a sample solution, the light intensity change (pulse form signal) of the light from a light-emitting particle other than the particle to be observed would be erroneously detected as the particle to be observed, resulting in the deterioration of the accuracy of the measurement result. Also, in the optical measurement techniques, such as FCS, FCCS, and FIDA, similarly, if a light-emitting particle, other than a particle to be observed, having the same emission wavelength as the particle to be observed is present, the contribution of the components other than the particle to be observed would be superimposed on the measured time series light intensity data so that the accuracy of the measurement result would deteriorate.

In order to avoid the deterioration of the measurement accuracy as described above, it is preferable that, on the measured light intensity data, the signal of light from a certain kind of light-emitting particle and the signal of light from another kind of light-emitting particle which have the same emission wavelength are discriminable, or that the signal of light from a particle to be observed and the signal of light from a light-emitting particle other than the particle to be observed are discriminable so that the signal of light from the light-emitting particle other than the particle to be observed is selectively removable. In this respect, as understood from the explanation relating to the above-mentioned scanning molecule counting method, in the present optical measurement technique which associates the optical system of a confocal microscope or a multiphoton microscope with a super-high sensitive light detection technique, it is possible to detect individually a light intensity change or a pulse form signal corresponding to each light-emitting particle appearing on a time series light intensity data measured with time progress. Therefore, the method of detecting a signal of each light-emitting particle individually may be utilized for the discrimination between a signal of light from a certain kind of a light-emitting particle and a signal of light from another kind of a light-emitting particle, the discrimination between a signal of light from a particle to be observed and a signal of light from a light-emitting particle other than the particle to be observed or the selective elimination of a signal of light from a light-emitting particle other than a particle to be observed on a time series light intensity data.

Thus, one object of the present invention is to propose a new method which makes it possible to detect individually and identify a light intensity change or a signal corresponding to light from a light-emitting particle in a sample solution in which light-emitting particles of two or more kinds having a common emission wavelength exist in a method of combining the optical system of a confocal microscope or a multiphoton microscope with a super-high sensitive light detection technique to measure light as described above.

In addition, in a method of measuring light as described above, it is more preferable not only to identify a signal corresponding to the light from a certain kind of a light-emitting particle selectively on a light intensity data, but also to make it possible to judge individually which kind of light-emitting particle a signal appearing on time series light intensity data corresponds to, e.g. whether a signal corresponds to a particle to be observed or to a light-emitting particle other than the particle to be observed. Thus, another object of the present invention is to propose a novel method which makes it possible to judge which kind a signal appearing on the measured light intensity data is of among two or more kinds of light-emitting particle in a method of combining the optical system of a confocal microscope or a multiphoton microscope with a super-high sensitive light detection technique to measure light as described above.

Solution to Problem

According to the present invention, the above-mentioned object is achieved by a method of detecting and analyzing light from a sample solution containing light-emitting particles of two or more kinds moving at random using an optical system of a confocal microscope or a multiphoton microscope characterized by comprising steps of measuring intensities of lights of two or more wavelength bands from a light detection region of the optical system in the sample solution simultaneously and by the wavelength band to generate a time series light intensity data individually for each of the wavelength bands; and detecting signals indicating light from a light-emitting particle and simultaneously generated on the time series light intensity data of at least two wavelength bands among the two or more time series light intensity data, and identifying the simultaneously generated signals as signals of a light-emitting particle of at least one specific kind among the two or more kinds of light-emitting particle. In this structure, "light-emitting particles . . . moving at random" may be particles, such as atoms, molecules or aggregates of these, which are dispersed or dissolved in a sample solution and emit light, and those may be arbitrary particulate matters making the Brownian motion freely in a solution without being fixed on a substrate, etc. The light-emitting particles are typically fluorescent particles, but may be particles which emit light by phosphorescence, chemiluminescence, bioluminescence, light scattering, etc. The "light detection region" of the optical system of the confocal microscope or multiphoton microscope is the micro region where light is detected in those microscopes, which region corresponds to the region to which illumination light is condensed when the illumination light is given from an objective (Especially in a confocal microscope, this region is determined in accordance with the spatial relationship of an objective and a pinhole. For a light-emitting particle which emits light without illumination light, for example, a molecule which emits light according to chemiluminescence or bioluminescence, no illumination light is required in the microscope.). Moreover, it should be understood that, in the meaning of "a light-emitting particle of at least one specific kind", which is made correspond to "simultaneously generated signals", not only a light-emitting particle of one kind but also a light-emitting particle of several kinds among the kinds contained in the sample solution may be included. (Further, in the followings in this specification, "a signal" means "a signal expressing light from a light-emitting particle" unless noted otherwise.)

Briefly speaking, in the above-mentioned inventive method, in a case that the light measurement and analysis are conducted for a sample solution containing light-emitting particles of two or more kinds using the optical system of a confocal microscope or a multiphoton microscope, first, light intensities of two or more wavelength bands are measured simultaneously and by the wavelength band, and each of signals simultaneously generated on the data of at least two wavelength bands among the time series light intensity data of two or more wavelength bands produced by this measurement is detected individually, so that a period in which simultaneously generated signals exist and a period in which no simultaneously generated signals exist will be identified in the time series light intensity data. It is considered that, in the period in which the simultaneously generated signals exist, a light-emitting particle having emission wavelength bands in all the at least two wavelength bands has entered into the light detection region, and therefore, it can be judged that, in that period, a light-emitting particle of at least one specific kind among two or more kinds of light-emitting particle was encompassed in the light detection region, so that the simultaneously generated signals may be identified as signals of a light-emitting particle of the at least one specific kind among two or more kinds of light-emitting particle. And, when it is grasped beforehand in which wavelength band a particle to be an observation object emits light, it becomes possible to identify whether the simultaneously generated signals are the signals of a particle to be observed or the signals of a light-emitting particle other than the particle to be observed. Namely, if the light of a particle to be observed is to be detected only in one wavelength band, the data of the generation period of signals simultaneously generated on the time series data of at least two wavelength bands can be identified not as a signal of the particle to be observed, and contrarily, if the light of a particle to be observed is to be detected in at least two wavelength bands, the data of the generation period of the simultaneously generated signals can be identified as signals of the particle to be observed.

In a structure of the present invention, the detection of signals simultaneously generated on time series data of at least two wavelength bands may be conducted, for instance, in a manner that, when the generation period of a signal indicating light of a light-emitting particle in a time series light intensity data of a first wavelength band among two or more wavelength bands overlaps the generation period of a signal indicating light of a light-emitting particle in the time series light intensity data of at least one wavelength band other than the first wavelength band among the two or more wavelength bands, the signal in the time series light intensity data of the first wavelength band and the signal in the time series light intensity data of the at least one wavelength band other than the first wavelength band are detected as simultaneously generated signals. For example, in a measurement of light, in a case that the number of measured bands is two, when the generation period of a signal in a time series light intensity data of one wavelength band overlaps the generation period of a signal in the time series light intensity data of another wavelength band, these signals may be judged as simultaneously generated signals. Further, in a case that the number of measured wavelength bands is three or more, when the generation period of a signal in a time series light intensity data of one wavelength band of the three or more bands overlaps the generation period of a signal in a time series light intensity data of one wavelength band among the remaining two or more wavelength bands, these signals may be judged as simultaneously generated signals; when the generation period of a signal in a time series light intensity data of one wavelength band overlaps all of the generation periods of signals in the time series light intensity data of two or more wavelength bands among the remaining two or more wavelength bands, these signals may be judged as simultaneously generated signals; or when the generation periods of signals in the time series light intensity data of all the wavelength bands overlap one another, these signals may be judged as simultaneously generated signals. That is, it should be understood that the combinations of wavelength bands to be seen in the judging of simultaneously generated signals may be arbitrarily chosen. And, it should also be understood that the number of discriminable kinds of light-emitting particle is determined by the number of the combinations of wavelength bands to be seen, and the number of the discriminable kinds of light-emitting particle increases as the number of the combinations of the wavelength bands to be seen increases.

In one manner, the above-mentioned inventive structure may be applied in an optical analysis method of detecting individually signals indicating light from light-emitting particles on time series light intensity data. In this case, in the inventive structure, there may be conducted a step of detecting individually a signal indicating light from a light-emitting particle on each of the time series light intensity data of two or more wavelength bands. And the kind of the light-emitting particle which emitted the light indicated by each detected signal may be identified based upon whether or not each signal has been generated simultaneously in at least two selected wavelength bands among the two or more wavelength bands. That is, according to this structure, it becomes possible to classify the signals which have appeared in the time series light intensity data according to a kind of light-emitting particle.

As above, when it has become possible to classify signals which have appeared in time series light intensity data according to a kind of light-emitting particle, it becomes possible to identify and classify each signal which have appeared in time series light intensity data in accordance with whether each signal is a signal of a particle to be observed or a signal of a particle other than the particle to be observed. Accordingly, in one manner, signals simultaneously generated in at least two selected wavelength bands may be identified as signals of a particle to be observed among two or more kinds of light-emitting particle while a signal indicating light from a light-emitting particle other than the simultaneously generated signals is identified as a signal of a light-emitting particle other than the particle to be observed; or contrarily, signals simultaneously generated in at least two selected wavelength bands may be identified as signals of light-emitting particles other than the particle to be observed among two or more kinds of light-emitting particle while a signal indicating light from a light-emitting particle other than simultaneously generated signals is identified as a signal of a particle to be observed. Especially in a case of measurement in two wavelength bands, signals simultaneously generated on the time series light intensity data of two wavelength bands may be identified as signals of a particle to be observed while a signal indicating light from a light-emitting particle has been generated only in one of the time series light intensity data of two wavelength bands is identified as a signal of a light-emitting particle other than the particle to be observed, or, signals simultaneously generated on time series light intensity data of two wavelength bands may be identified as signals of a light-emitting particle other than a particle to be observed while a signal indicating light from a light-emitting particle has been generated only in one the time series light intensity data of two wavelength bands is identified as a signal of the particle to be observed.

Further, the above-mentioned structure of the present invention may be applied to the scanning molecule counting method as described above. That is, in one aspect of the inventive method, there may be conducted steps of measuring light intensities of two or more wavelength bands from a light detection region with moving the position of the light detection region in a sample solution by changing the optical path of the optical system of a confocal microscope or a multiphoton microscope, and detecting individually each signal indicating light from a single light-emitting particle in each of the obtained time series light intensity data, wherein, as noted above, for each of the detected signals, the kind of light-emitting particle which emitted the light indicated by the signal is identified based on whether or not each signal has been simultaneously generated in at least two selected wavelength bands among the two or more wavelength bands.

In the basic structure of the scanning molecule counting method to which the present invention is applied, first, after preparing a sample solution containing light-emitting particles by an arbitrary method, the measurement of light intensity is sequentially performed while the position of a light detection region is moved in the sample solution, namely, while the inside of the sample solution is scanned with the light detection region. Then, when the moving light detection region encompasses a randomly moving light-emitting particle, the light from the light-emitting particle is detected by the light detecting portion, and thereby, the existence of one particle will be detected. And, in the time series light intensity data indicating sequentially detected light, a signal indicating light from a light-emitting particle is individually detected, and thereby, the individual existences of light-emitting particles are detected one by one, and accordingly, diverse information on the condition of a particle in the solution will be acquired. In this connection, in detecting individually a signal indicating light from a single light-emitting particle, the detection of a signal corresponding to one light-emitting particle on the time series light intensity data may be done based on the shape of the signal detected in time series. In one embodiment, typically, when a pulse form signal which has a higher intensity than a predetermined threshold value is detected, its signal is a signal corresponding to one light-emitting particle, and thus, it may be detected that one light-emitting particle was present in the light detection region in the generation period of the signal. Further, in the case of the present invention, it has become possible to identify the kind of light-emitting particle corresponding to each signal based on whether or not the respective signals have been simultaneously generated in at least two selected wavelength bands among two or more wavelength bands, or to classify an individual signal corresponding to a light-emitting particle based on its emission wavelength band, and therefore it becomes possible to extract only the signal of a light-emitting particle of a certain selected emission wavelength band, or to extract a signal by the group of the signals classified based on the emission wavelength bands.

Furthermore, as already noted, since it will also become possible to identify signals simultaneously generated in at least two selected wavelength bands as signals of a particle to be observed (or signals of a light-emitting particle other than the particle to be observed) among light-emitting particles of two or more kinds and to identify a signal other than the simultaneously generated signals as a signal of a light-emitting particle other than the particle to be observed (or as a signal of the particle to be observed), it becomes possible in a scanning molecule counting method to identify and detect a signal of a particle to be observed and a signal of a light-emitting particle other than the particle to be observed, and thus, the exclusion of signals of light-emitting particles other than the particle to be observed will become possible, and thereby the deterioration of the accuracy of measurement can be avoided. Also in the case of measurement in two wavelength bands, signals simultaneously generated on the time series light intensity data of two wavelength bands may be identified as signals of a particle to be observed while a signal generated only in one of the time series light intensity data of two wavelength bands is identified as a signal of a light-emitting particles other than the particle to be observed, or signals simultaneously generated on the time series light intensity data of two wavelength bands may be identified as signals of a light-emitting particle other than a particle to be observed while a signal generated only on one of the time series light intensity data of two wavelength bands is identified as a signal of a particle to be observed. In this regard, signals simultaneously generated on the time series light intensity data of two wavelength bands, a signal generated only in one of the time series light intensity data of two wavelength bands and a signal generated in the other of the time series light intensity data of two wavelength bands may be identified as the mutually different particles to be observed (Namely, three kinds of light-emitting particles may be identified.).

In the execution of the scanning molecule counting method in the present invention, the number of the light-emitting particles detected during the moving of the position of the light detection region may be counted by counting the number of the individually detected signals indicating light from single light-emitting particles (The Counting of particles). In that case, by associating the number of light-emitting particles with the moving amount of the position of the light detection region, the information on the number density or concentration of the light-emitting particle in the sample solution will be acquired. Especially, by determining the whole volume of the moving track of the position of the light detection region by an arbitrary method, for example, by moving the position of the light detection region at a predetermined speed, the number density or concentration of the light-emitting particle can be concretely computed. Of course, instead of determining directly the absolute number density value or concentration value, the relative ratio of the number density or concentration to a plurality of sample solutions or a standard sample solution to be a reference of a concentration or a number density may be computed. Moreover, in the above-mentioned present invention, since the position of the light detection region is moved by changing the optical path of an optical system, the movement of the light detection region is quick without substantial generation of mechanical vibration and hydrodynamic effect in the sample solution, and therefore, the measurement of light can be performed under a stable condition without dynamic action affecting the light-emitting particle in the sample solution (without artifact) (For example, when a flow is generated in the sample, not only making the flow velocity always uniform is difficult, but also the device structure would become complicated, and furthermore, not only the required sample amount is substantially increased, but also it is possible that light-emitting particles or other substances in a solution would deteriorate or be denaturalized by the hydrodynamic action of the flow.). Further, since no structure for flowing a sample solution is required, the measurement and analysis can be conducted with a small amount of the sample solution (at the level of one to several tens of µL) similarly to FCS and FIDA, etc.

Moreover, in moving the position of the above-mentioned light detection region, the moving speed of the position of the light detection region in the sample solution is appropriately changed based on the characteristic or the number density or concentration of the light-emitting particle in the sample solution. As understood by ones ordinarily skilled in the art, the condition of detected light from the light-emitting particle may change in accordance with its characteristic, number density or concentration in the sample solution. Especially, when the moving speed of the light detection region becomes quick, the amount of light obtained from one light-emitting particle will be reduced, and therefore it is preferable that the moving speed of the light detection region can be changed appropriately so that the light from one light-emitting particle (especially, a particle to be observed) can be measured precisely or with sufficient sensitivity.

Furthermore, in the above-mentioned step of moving the position of the light detection region, the moving speed of the position of the light detection region in the sample solution is preferably set to be higher than the diffusional moving velocity of a light-emitting particle (the average moving speed of a particle owing to the Brownian motion). As explained above, in the inventive method, the light emitted from a light-emitting particle is detected in the light detection region, so that the light-emitting particle will be detected individually. However, when a light-emitting particle moves at random owing to the Brownian motion to move into and out of the light detection region multiple times, the signal from one light-emitting particle (showing its existence) will be detected multiple times, and therefore it would become difficult to make the existence of one light-emitting particle associated with the detected signal. Then, as described above, the moving speed of the light detection region is set higher than the diffusional moving velocity of the light-emitting particle, and thereby it becomes possible to make one light-emitting particle correspond to one signal (indicating the existence of a particle). In this regard, since the diffusional moving velocity differs depending upon a light-emitting particle, it is preferable that the moving speed of the light detection region can be changed appropriately according to the characteristics (especially, the diffusion constant) of the light-emitting particle as described above.

The changing of the optical path of the optical system for moving the position of the light detection region may be done in an arbitrary way. For example, the position of the light detection region may be changed by changing the optical path using a galvanomirror employed in the laser scan type optical microscope. The movement track of the position of the light detection region may be set arbitrarily, for example, which is selectable from circular, elliptical, rectangular, straight and curvilinear ones.

Furthermore, according to the present invention, since simultaneously generated signals among signals indicating light from a light-emitting particle detected on time series light intensity data of two or more wavelength bands are detected and the discrimination between simultaneously generated signals and other signals is made, the counting and determination of the concentration or number density of particles can be performed for the light-emitting particle corresponding to the simultaneously generated signals and the other light-emitting particle separately, and thereby, it becomes possible to reduce the influence of unnecessary data or to ignore or delete them, and accordingly, it is advantageous in conducting the observation and analysis of the light-emitting particle of a specific kind in a sample solution, and the observation and analysis of the interaction of the light-emitting particles in the sample solution.

By the way, the above-mentioned inventive method may be used for arbitrary optical analysis methods other than the scanning molecule counting method. Especially in a case that it is not required to identify individual signals of particles to be observed of two or more kinds of light-emitting particles, signals simultaneously generated in at least two wavelength bands selected from two or more wavelength bands are identified as signals of a light-emitting particle other than the particle to be observed of the two or more kinds of light-emitting particle, and thereby, it becomes possible to extract only the signals of light-emitting particles other than the particle to be observed to ignore or exclude them in various analyses. Moreover, depending upon manners of optical analysis methods to be performed, in a case that it is possible to delete or remove, from time series light intensity data, the data in a generation period of simultaneously generated signals, i.e., the data of a period in which the light from a light-emitting particle other than a particle to be observed has been measured, the data of a generation period of signals identified in time series light intensity data as the signals of a light-emitting particle other than a particle to be observed may be removed. Such an optical analysis method may be an optical analysis using time series light intensity data indicating light intensity from particles to be observed, for instance, Fluorescence correlation spectroscopy (FCS), Fluorescence intensity distribution analysis method (FIDA) or Fluorescence cross correlation spectroscopy (FCCS). According to this structure, it becomes possible to conduct an analysis with the data of a period in which a light-emitting particle other than a particle to be observed is present in the light detection region being eliminated selectively, so that deterioration of the accuracy of results will be prevented.

The inventive method is used, typically, for an analysis of a condition in a solution of a biological particulate object, such as a biological molecule, e.g. a protein, a peptide, a nucleic acid, a lipid, a sugar chain, an amino acid or these aggregate, a virus and a cell, etc., but it may be used for an analysis of a condition in a solution of a non-biological particle (for example, an atom, a molecule, a micelle, a metallic colloid, etc.), and it should be understood that such a case belongs to the scope of the present invention also.

Effect of Invention

As described above, in the inventive method, by detecting individually signals simultaneously generated in at least two selected wavelength bands in the time series light intensity data obtained by the light measurement of two or more wavelength bands using an optical system of a confocal microscope or a multiphoton microscope, it becomes possible to identify, on the time series light intensity data, the individual period in which a light-emitting particle emitting the light of the selected wavelength bands has been present in the light detection region of the optical system of the confocal microscope or multiphoton microscope, and thus, even for mutually different light-emitting particles which have a partially common emission wavelength band so that no discrimination between them can be made from the light measurement in only the wavelength, it becomes possible to grasp when the light from such a light-emitting particle has been detected on the time series light intensity data. And, according to this structure, since it is possible to extract signals of a certain specific kind of light-emitting particle (light-emitting particle which emits the light of the selected wavelength band) and its generation period, the selection of the respective data or the classification of data on the time series light intensity data can be performed. Thus, for example, when simultaneously generated signals are identified as significant signals in a measurement or contrarily when simultaneously generated signals are identified as a noise in measurement, etc., signal-noise separation may be attained in high accuracy. Especially, in a case that simultaneously generated signals are identified as noise in measurement, etc., the removing of noise from time series light intensity data is possible, and therefore, the present invention is advantageously usable as one means for the noise rejection in analyses, such as FCS, FIDA, PCH, and FCCS.

Moreover, in applying the inventive method to the scanning molecule counting method, detection of a light-emitting particle and counting of particles become more accurately achievable. With respect to the light detecting mechanism itself, the scanning molecule counting method is designed to detect light from the light detection region of a confocal microscope or a multiphoton microscope similarly to cases of optical analysis techniques such as FCS, FCCS, and FIDA, and therefore, the amount of a sample solution may be similarly small, and in addition, since no statistical procedures, such as computing the fluctuation of fluorescence intensity, is performed, it is applicable to a sample solution in which the number density or concentration of a particle is substantially lower than the level required for optical analysis techniques, such as FCS, FCCS and FIDA. When the structure of the inventive method is further incorporated in such a scanning molecule counting method to make it possible to discriminate between signals simultaneously generated in at least two selected wavelength bands and the other signals, it is expected that a specific light-emitting particle or a particle to be an object to be observed becomes detectable and the accuracy of the counting will also be improved even in a case that the concentration of the light-emitting particle in a sample solution is significantly lower than the level required for optical analysis techniques, such as FCS, FCCS, and FIDA, and a certain specific light-emitting particle and the other light-emitting particle having the same emission wavelength band as the former one co-exist in the sample solution so that they can not be discriminated in a measurement of the light of only that wavelength band, or in a case that the number or concentration of a light-emitting particle to be an object to be observed is relatively low as compared with the number or concentration of the other light-emitting particles or contaminants so that the light of the particle to be observed will be buried in the light intensity data in conventional light measurement techniques where light intensity is continuously measured. For example, the present invention may be applied to a case of observing a light-emitting particle at a low-concentration in a sample solution including many particles causing noise (plasma sample etc.).

Furthermore, according to the structure incorporating the inventive method in the scanning molecule counting method, it becomes possible to detect, in a sample solution containing light-emitting particles of two or more kinds having mutually different emission wavelength bands, the presence or absence of the interaction of those light-emitting particles with high accuracy. According to the present invention, signals simultaneously generated on time series light intensity data of two or more wavelength bands are detected individually, and therefore, even in a case that the interaction of light-emitting particles of two or more kinds in a sample solution is weak and only a small amount of the combination of those light-emitting particles is formed (for example, at the level where the detection in FCCS is difficult), the detection of the existence of the combination, the counting thereof, etc. can be achieved.

Other purposes and advantages of the present inventions will become clear by explanations of the following preferable embodiments of the present invention.

BRIEF DESCRIPTIONS OF DRAWINGS

FIG. 1A is a schematic diagram of the internal structure of the optical analysis device with which the present invention is performed. FIG. 1B is a schematic diagram of a confocal volume (an light detection region of a confocal microscope). FIG. 1C is a schematic diagram of the mechanism for changing the direction of the mirror 7 to move the position of a light detection region in a sample solution.

FIGS. 2A and 2B are a schematic diagram explaining the principle of the light detection and a schematic diagram of the variation of the measured light intensity with time in the scanning molecule counting method to which the inventive method is applied, respectively.

Figure 3A:
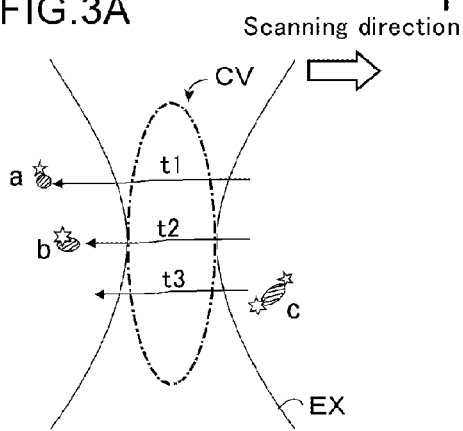
Figure 3B:
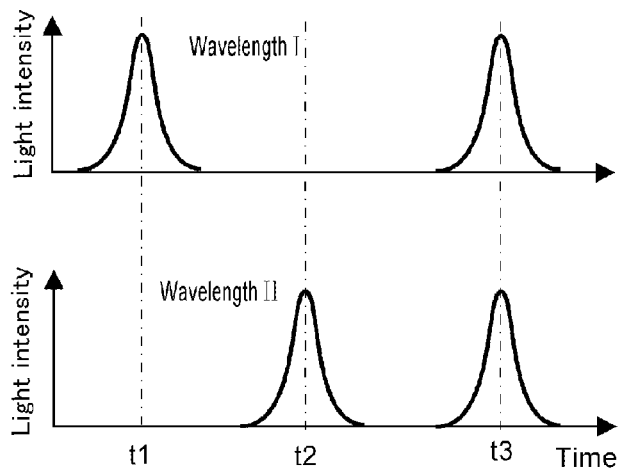
Figure 3C:
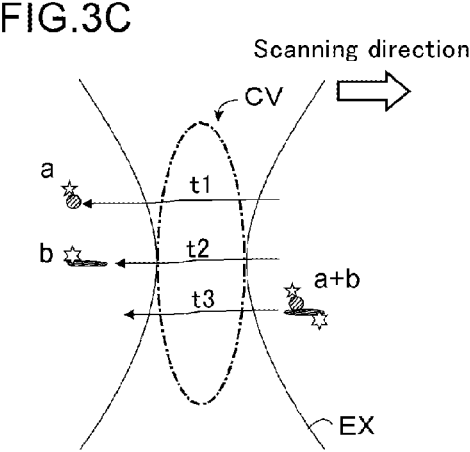
Figure 3D:
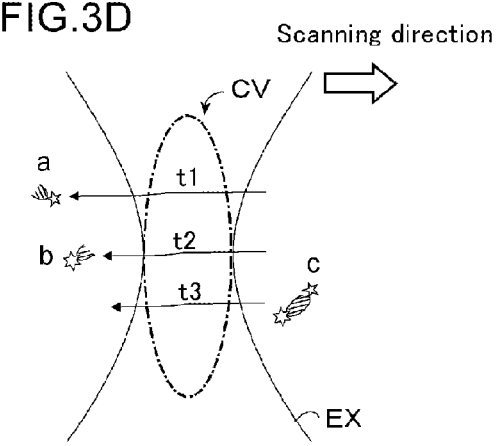
Figure 3E:
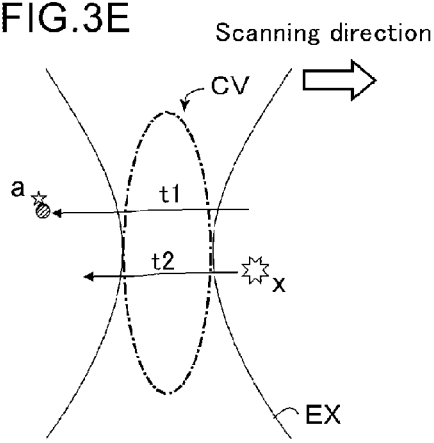
Figure 3F:
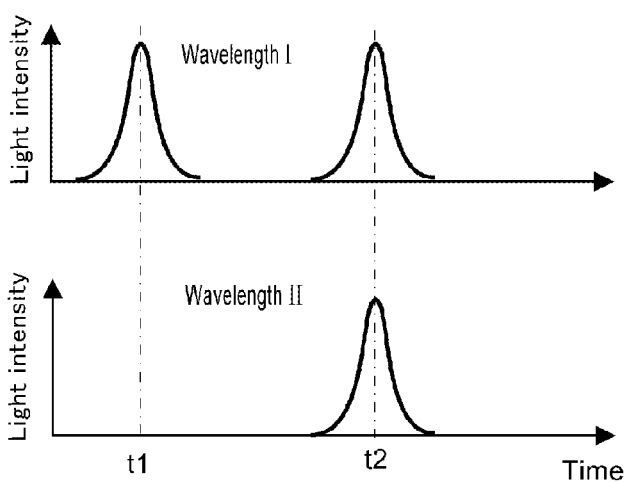

FIGS. 3A, 3C, 3D, and 3E are the drawings showing schematically examples of the combinations of light-emitting particles to be identified by detecting signals simultaneously generated on the light intensity data measured in two or more wavelength bands. FIG. 3B shows schematic diagrams of the time variations of the light intensities measured in FIGS. 3A, 3C and 3D (time series light intensity data), and FIG. 3F shows schematic diagrams of the time variations of the light intensities measured in FIG. 3E (time series light intensity data).

Figure 4:
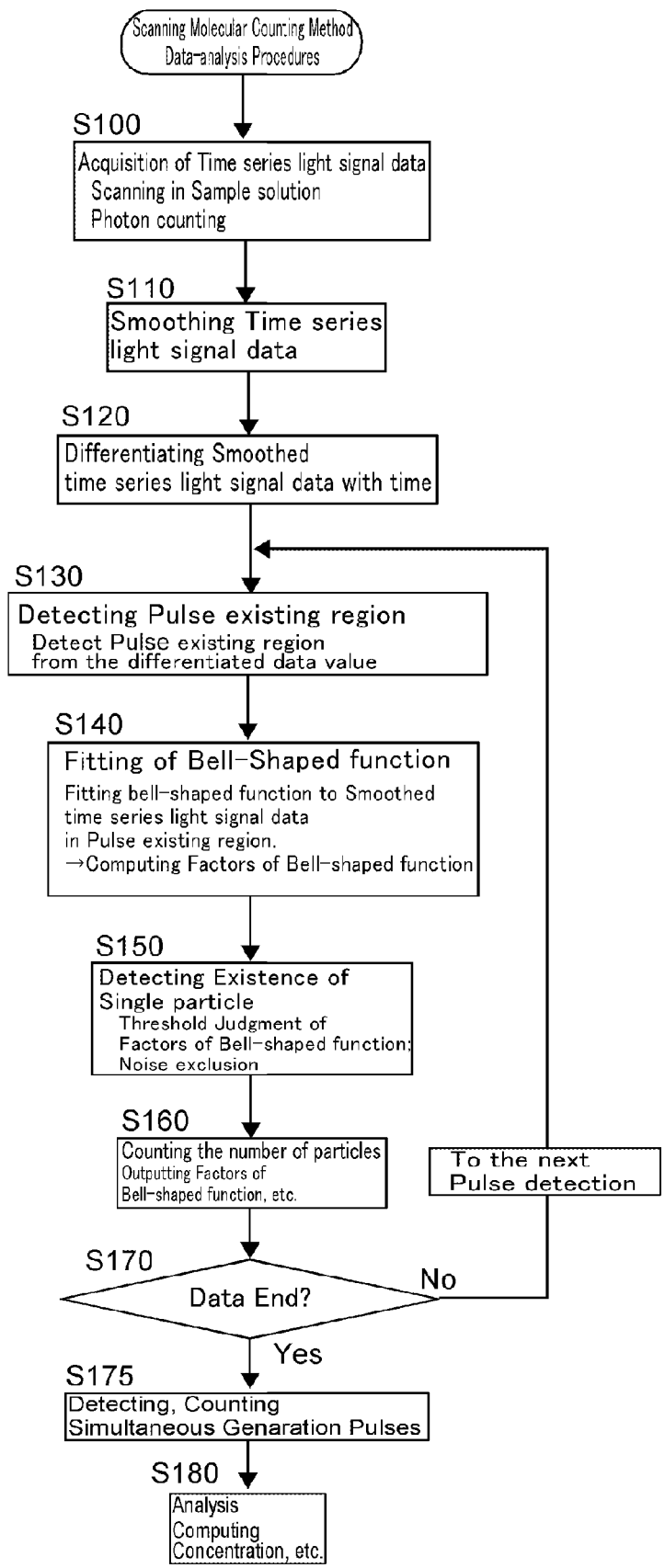

FIG. 4 is a drawing showing the procedures in the form of a flow chart of the scanning molecule counting method of performing a measurement of light in two or more wavelength bands and the detection and the counting of signals simultaneously generated in two or more wavelength bands in accordance with the inventive method.

FIGS. 5A and 5B are drawings of models in a case that a particle to be observed crosses a light detection region owing to Brownian motion and in a case that a particle to be observed crosses a light detection region by the moving of the position of the light detection region in a sample solution at a velocity quicker than the diffusional moving velocity of the particle to be observed. FIG. 5C shows drawings explaining the example of the signal processing step of the detected signals in the procedure for detecting the existence of a light-emitting particle from the measured time series light intensity data (change in time of a photon count) in accordance with the scanning molecule counting method.

Figure 6A:
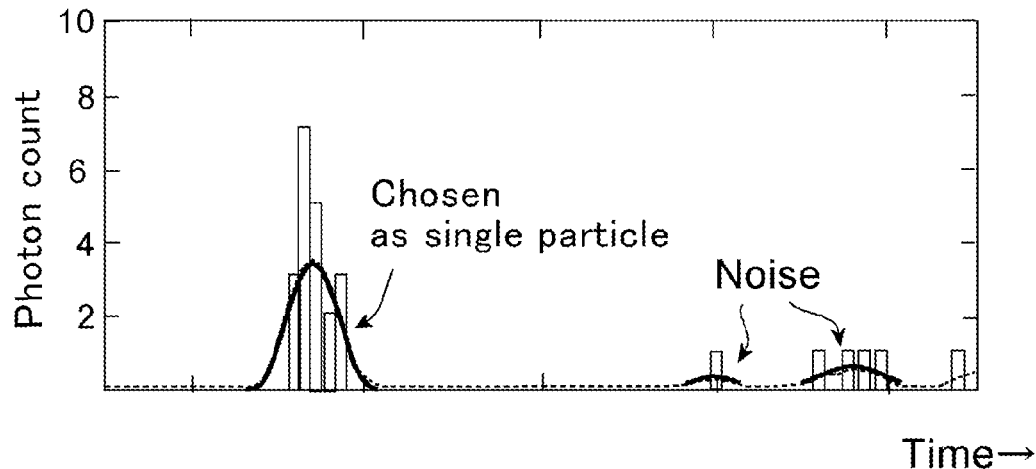
Figure 6B:
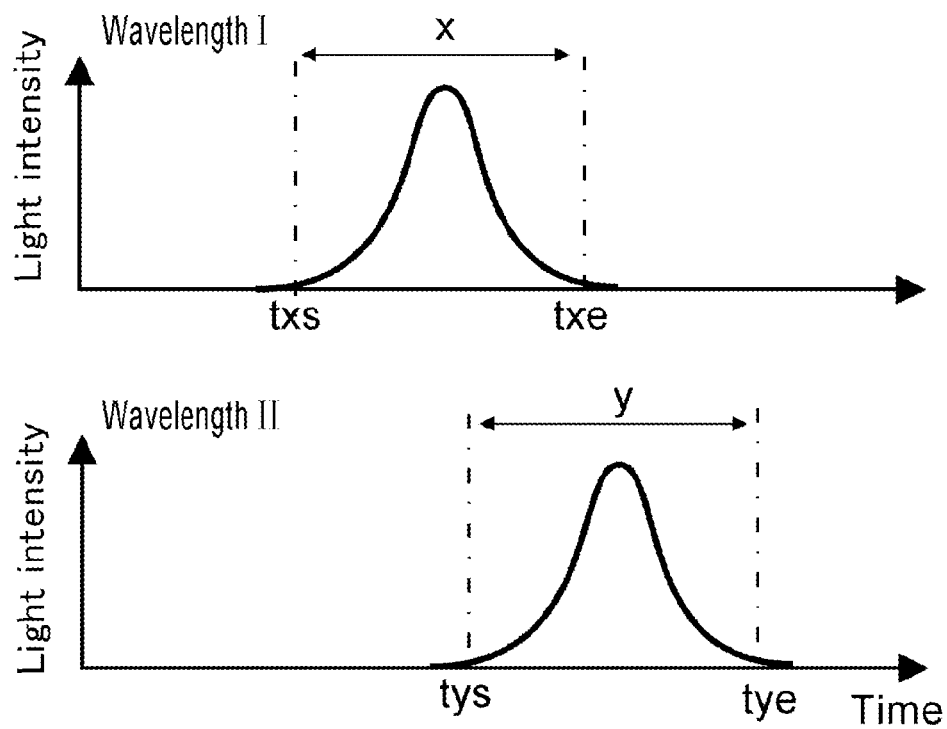

FIG. 6A shows examples of measured photon count data (bar graph); curves obtained by carrying out the smoothing of the data (dotted line); and Gauss functions fitted on the pulse existing regions (solid line). In the drawing, the signals attached with "noise" are disregarded as signals due to noises or a contaminant. FIG. 6B is a drawing explaining the process of judging whether or not signals generated in the time series light intensity data of different wavelength bands have been simultaneously generated.

FIG. 7A is a drawing showing the procedures in the form of a flow chart in a case that measurement of light of two or more wavelength bands, detection of signals simultaneously generated in two or more wavelength bands and removal of generation periods of noise, etc. from time series light intensity data are performed and then an analysis, such as FCS etc. are performed. FIG. 7B are diagrams explaining the process of detecting signals simultaneously generated in two or more measured wavelength bands to specify a generation period of noise, etc.

FIGS. 8A-8D show an example of light intensity data (photon count data) in two wavelength bands (the upper two rows), data after smoothing of the light intensity data (the middle row) and pulses identified in the fitting of a bell shaped function (pulse form signals) (the lower row) obtained in the scanning molecule counting method performed in accordance with the inventive method. (in the case of Embodiment 1).

Figure 9A:
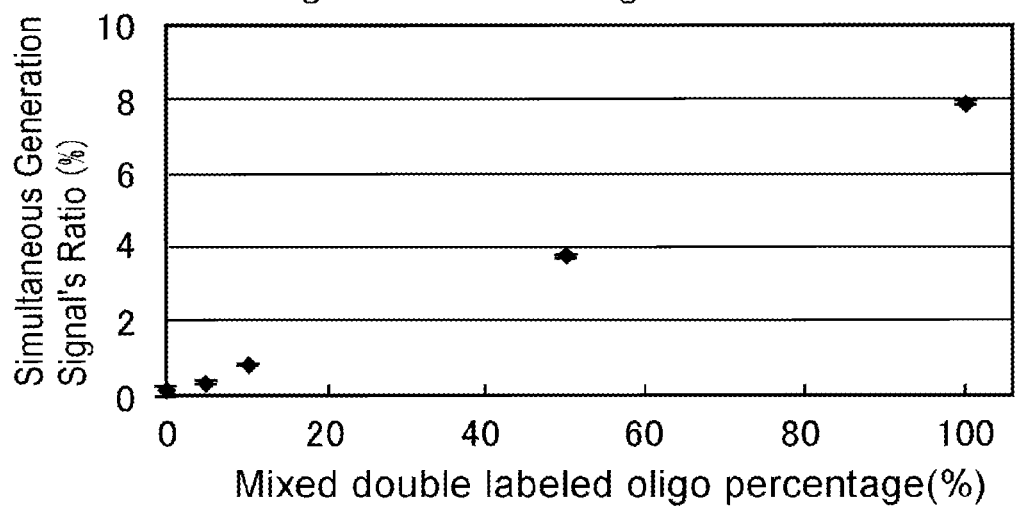
Figure 9B:
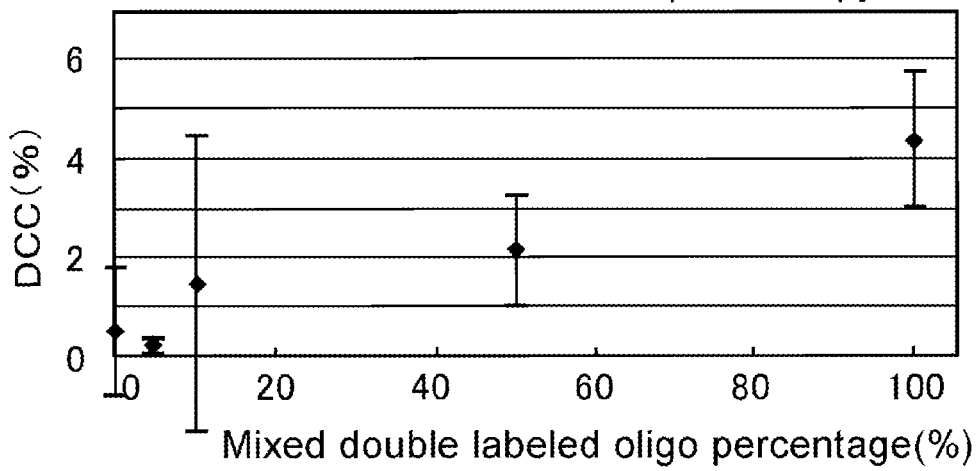

FIG. 9A shows the results in the detection experiment of oligonucleotide labeled with two differently colored fluorescent dyes obtained in the case of Embodiment 1 performed in accordance with the inventive method, and FIG. 9B shows the results in the detection experiment of oligonucleotide labeled with two differently colored fluorescent dyes obtained in FCCS, respectively. The error bar in each plot shows the width of the three times of the SD value in three measurements.

Figure 10:
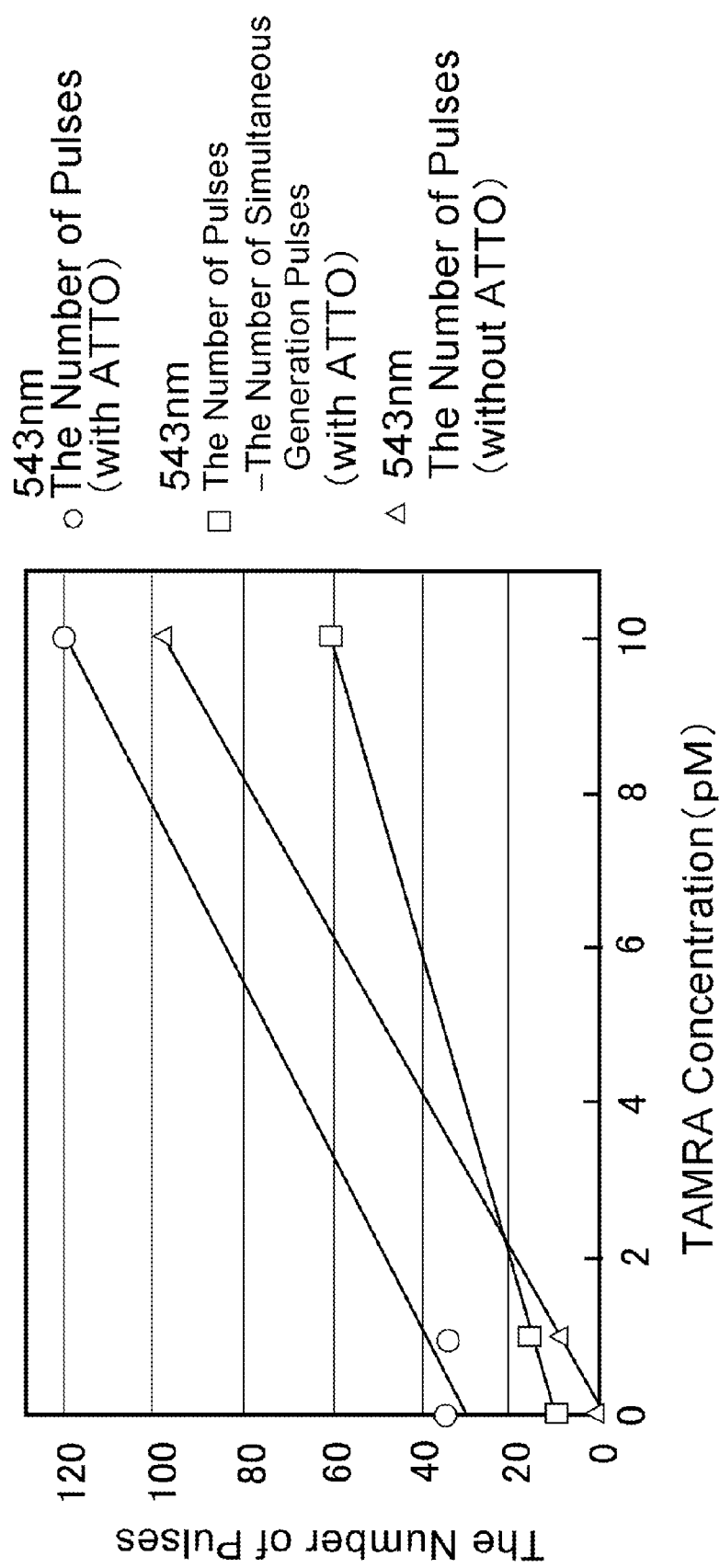

FIG. 10 shows the results of the counting of light-emitting particles of one kind (fluorescent dye molecule TAMRA) in a sample solution containing two or more kinds of light-emitting particle, obtained in the scanning molecule counting method performed in accordance with the inventive method (Embodiment 2).

Figure 11A:
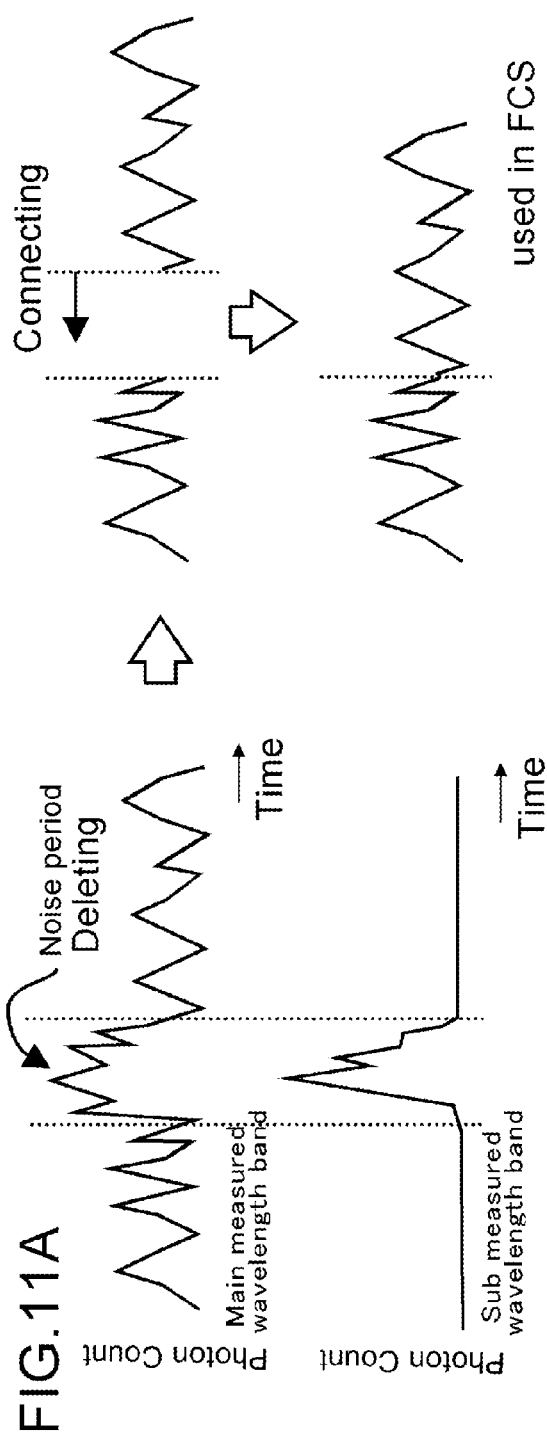
Figure 11B:
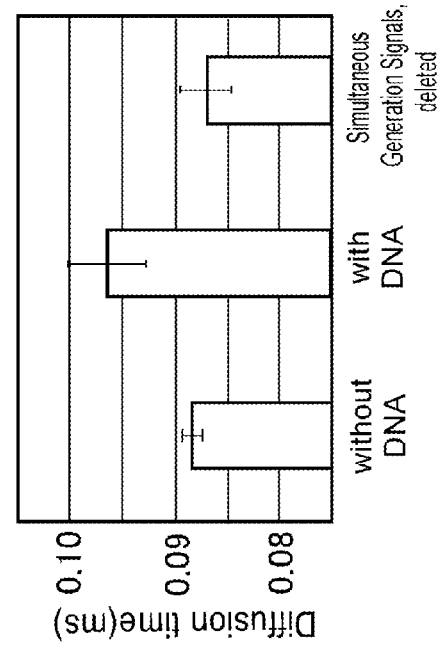
Figure 11C:
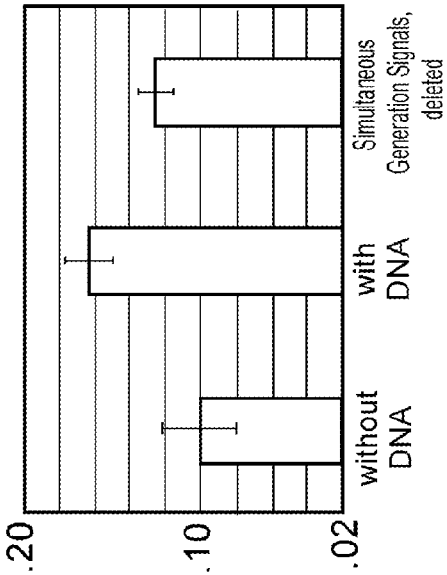

FIG. 11A schematically shows the steps in FCS (Embodiment 3) performed with the application of the inventive method, where, after deleting, from the time series light intensity data of the main measured wavelength band, the data of the period corresponding to a period judged as a noise period in the time series light intensity data of the sub measured wavelength band, the data being continuous in time are reconstructed. FIGS. 11B and 11C show the results of the particle count and translational diffusion time of a light-emitting particle (fluorescent dye molecule ATTO) obtained in FCS (embodiment 3) performed with the application of the inventive method. The error bars in the drawings show the three times of SD values.

FIGS. 12A, 12B show examples of the time variation of the photon count (light intensity) obtained in a conventional optical analysis technique computing fluorescence intensity fluctuation, where FIG. 12A shows a case that the particle concentration is at a level providing a sufficient precision in the measurement, and FIG. 12B shows a case that the particle concentration in a sample is significantly lower than the case of FIG. 12A.

EXPLANATIONS OF REFERENCE NUMERALS

1—Optical analysis device (confocal microscope)
2—Light source
3—Single mode optical fiber
4—Collimating lens 5, 14a—Dichroic mirror
6, 7, 11—Reflective mirror
8—Objective
9—Micro plate
10—Well (sample solution container)
12—Condenser lens
13—Pinhole
14—Barrier filter
15—Multi-mode optical fiber
16—Photodetector
17—Mirror deflector
17a—Stage position changing apparatus
18—Computer

DESCRIPTION OF EMBODIMENTS

In the followings, preferable embodiments of the present invention are described in detail.

The Structure of an Optical Analysis Device

The method of the present invention may be conducted while being incorporated in an optical analysis method, such as scanning molecule counting method or FCS, FCCS, FIDA, etc. In this respect, especially in the inventive method, the measurement and analysis of the lights of two or more mutually different wavelength bands are performed, and therefore, the inventive method can be realized with an optical analysis device 1 formed by combining an optical system of a confocal microscope and a photodetector as schematically illustrated in FIG. 1A with which an optical analysis method, such as the scanning molecule counting method or FCS, FCCS and FIDA, are realizable, and the measurement of the lights of mutually different wavelength bands is performable.

Concretely, referring to FIG. 1A, the optical analysis device 1 consists of an optical system 2-17 and a computer 18 for acquiring and analyzing data together with controlling the operation of each part in the optical system. The optical system of the optical analysis device 1 may be the same as the optical system of a usual confocal microscope, where laser light emitted from a light source 2 and transmitted through the inside of a single mode fiber 3 (Ex) forms light diverging to be radiated at the angle decided by an inherent NA at the emitting end of the fiber; and after forming a parallel beam with a collimator 4, the light is reflected on a dichroic mirror 5 and reflective mirrors 6 and 7, entering into an objective 8. In this regard, in order that the wavelength of excitation light can be selected appropriately in accordance with the wavelength of the light exciting a light-emitting particle, as shown in the drawing, two or more light-emitting sources (laser) may be prepared in the light source 2. When the wavelengths of the excitation light for light-emitting particles to be observed simultaneously differ from one another, lights are simultaneously emitted from two or more light-emitting sources and introduced into the objective 8.

Above the objective 8, typically, there is placed a sample container or a micro plate 9 having wells 10 arranged thereon, to which one to several tens of μL of a sample solution is dispensed, and the laser light emitted from the objective 8 is focused in the sample solution in the sample container or well 10, forming a region having strong light intensity (excitation region). In the sample solution, light-emitting particles to be observed objects, which are typically molecules to which a light emitting label such as a fluorescent dye is attached, are dispersed or dissolved, and when a light-emitting particle enters into the excitation region, the light-emitting particle is excited and emits light during dwelling in the excitation region. The emitted light (Em), after passing through the objective 8 and the dichroic mirror 5, is reflected on the mirror 11 and condensed by a condenser lens 12, and then the light passes through the pinhole 13. In this regard, as known in ones skilled in the art, the pinhole 13 is located at a conjugate position of the focal position of the objective 8, and thereby only the light emitted from the focal region of the laser light, i.e., the excitation region, as schematically shown in FIG. 1B, passes through the pinhole 13 while the light from regions other than the focal plane is blocked. The focal region of the laser light illustrated in FIG. 1B is a light detection region, whose effective volume is usually about 1-10 fL, in this optical analysis device, which is called as "confocal volume". In the confocal volume, typically, the light intensity is spread in accordance with a Gaussian type or Lorentz type distribution having the peak at the center of the region, and the effective volume is a volume of an approximate ellipsoid bordering a surface where the light intensity is reduced to $1/e^2$ of the peak intensity.

Then, the light having passed through the pinhole 13 is divided in accordance with the wavelength band in the manner that the light of a part of wavelength bands is reflected on, and the light of the remaining wavelength bands penetrates through the dichroic mirror 14a, and each component of the divided lights transmits through the corresponding barrier filter 14 (where light components only in a specific wavelength band are selected); and is introduced into a multimode fiber 15, reaching to the corresponding photodetector 16, and after the conversion into time series electric signals, the signals are inputted into the computer 18, where the processes for optical analyses are executed in manners explained later. For the photodetectors 16, preferably, super high sensitive photodetectors, usable for the photon counting, are used, so that the light from one light-emitting particle, for example, the faint light from one or several fluorescent dye molecule(s), can be detected.

Especially in a case that a scanning molecule counting method is performed in the above-mentioned structure, there is further provided in the optical system of the above-mentioned optical analysis device a mechanism for changing the optical path of the optical system to scan the inside of the sample solution with the light detection region, namely to move the position of the focal region i.e., the light detection region, within the sample solution. For this mechanism for moving the position of the light detection region, for example, there may be employed a mirror deflector 17 which changes the direction of the reflective mirror 7, as schematically illustrated in FIG. 1C. This mirror deflector 17 may be the same as that of a galvanomirror device equipped on a usual laser scan type microscope. Also, in order to attain a desired moving pattern of the position of the light detection region, the mirror deflector 17 is driven in harmony with the light detection of the photodetector 16 under the control of the computer 18. The movement track of the position of the light detection region may be arbitrarily selected from circular, elliptical, rectangular, straight and curvilinear ones, or a combination of these (The program in the computer 18 may be designed so that various moving patterns can be selected.). In this regard, although not illustrated, the position of the light detection region may be moved in the vertical direction by moving the objective 8 up and down. As noted, according to the structure of changing the optical path of the optical system to move the position of the light detection region instead of moving the sample solution, neither mechanical vibration nor hydrodynamic action occur substantially in the sample solution, so that it becomes possible to eliminate the influence of a dynamic action on an object to be observed, achieving the stable measurement. In this connection, in a case that only an optical analysis method, such as FCS, FCCS, FIDA, etc., is performed, no mechanism for changing the direction of the reflective mirror 7 needs to be provided.

Also, for an additional structure, on the stage (not shown) of the microscope, there may be provided a stage position changing apparatus 17a for moving the horizontal position of the micro plate 9, in order to change the well 10 to be observed. The operation of the stage position changing apparatus 17a may be controlled by the computer 18.

In the case that a light-emitting particle emits light by multiple photon absorption, the above-mentioned optical system is used as a multiphoton microscope. In that case, since the light is emitted only from the focal region of the excitation light (light detection region), the pinhole 13 may be removed. Further, in the case that a light-emitting particle emits light owing to a chemiluminescence or bioluminescence phenomenon without excitation light, the optical system 2-5 for generating excitation light may be omitted. When a light-emitting particle emits light owing to phosphorescence or scattered light, the above-mentioned optical system of the confocal microscope is used as it is.

A. Embodiment of the Present Invention in Scanning Molecule Counting Method

As described in the column of "Summary of invention", in one aspect, the inventive method is advantageously realized in combination with Scanning molecule counting method. In the other words, it can be said that one embodiment of the present invention is the improvement of the scanning molecule counting method. In the following, the embodiment of the present invention in the scanning molecule counting method is described.

1. Principle of Scanning Molecule Counting Method

Spectral analysis techniques, such as FCS, FCCS, FIDA, etc., are advantageous in that the required sample amount is extremely small and a test can be performed promptly as compared with the conventional biochemical analytical techniques. However, in these spectral analysis techniques such as FCS, FCCS, FIDA, etc., the concentration and characteristics of a particle to be observed are principally computed based on the fluorescence intensity fluctuation, and therefore, in order to obtain accurate measurement results, the concentration or number density of the particle to be observed in a sample solution should be at a level where about one particle to be observed always exists in a light detection region CV during the fluorescence intensity measurement as schematically drawn in FIG. 12A so that significant light intensity (photon count) can be always detected in the measuring term as shown in the right-hand side of the drawing. When the concentration or number density of the particle to be observed is lower than that, for example, at the level where the particle to be observed rarely enters into the light detection region CV as drawn on FIG. 12B, no significant light intensity signal (photon count) would appear in a part of the measuring term as illustrated on the right-hand side of the drawing, and thus, accurate computation of light intensity fluctuation would become difficult. Also, when the concentration of the particle to be observed is significantly lower than the level where about one particle to be observed always exists in the inside of the light detection region during the measurement, the calculation of light intensity fluctuation would become subject to the influence of the background, and the measuring term should be made long in order to obtain the significant quantity of the light intensity data (photon count) sufficient for the calculation.

Then, in the Japanese patent application no. 2010-044714, and PCT/JP2011/53481, the applicant of the present application has proposed "Scanning molecule counting method" based on a new principle which enables the detection of characteristics of a particle to be observed, such as its number density or concentration, even when the concentration of the particle to be observed is lower than the level requested in the above-mentioned spectral analysis techniques, such as FCS and FIDA.

In the scanning molecule counting method, briefly speaking, as the processes to be performed, the light detection is performed together with moving the position of the light detection region CV in a sample solution, namely, scanning the inside of the sample solution with the light detection region CV by driving the mechanism (mirror deflector 17) for moving the position of the light detection region to change the optical path as schematically drawn in FIG. 2. Then, for example, as in FIG. 2A, during the moving of the light detection region CV (in the drawing, time to-t2), when the light detection region CV passes through a region where one light-emitting particle exists (t1), light is emitted from the light-emitting particle, and a pulse form signal having significant light intensity (Em) appears as drawn in FIG. 2B. Thus, by detecting, one by one, each pulse form signal (significant light intensity) appearing as illustrated in FIG. 2B during the execution of the moving of the position of the light detection region CV and the light detection as described above, the light-emitting particles are detected individually, and by counting the number thereof, the information about the number, concentration or number density of the light-emitting particles existing in the measured region can be acquired. In the principle of this inventive optical analysis technique, no statistical calculation processes, such as the calculation of the fluorescence intensity fluctuation, are conducted and the light-emitting particles are one by one detected, and therefore, the information about the concentration or number density of the particle is acquirable even in a sample solution with a low particle concentration at the level where no sufficiently accurate analysis is available in FCS, FCCS, FIDA, etc.

2. Manners of Discrimination of Two or More Kinds of Light-Emitting Particles in Accordance with the Invention In performing the scanning molecule counting method with incorporating the inventive method, first, in accordance with the above-mentioned principle, there is performed the measurement with time progress of light intensities (photon counting) in two or more wavelength bands individually and simultaneously for a sample solution containing light-emitting particles of two or more kinds, and a pulse form signal corresponding to a light-emitting particle is detected one by one in each of the measured time series light intensity data (photon counting data) of the wavelength bands, and after this, among the detected pulse form signals, pulse form signals simultaneously generated on time series light intensity data of at least two selected wavelength bands are detected. These simultaneously generated pulse form signals are considered to correspond to one light-emitting particle having emission wavelengths in all the selected wavelength bands (it is very rare that light-emitting particles having different emission wavelengths in the selected wavelength bands simultaneously jump into the confocal volume (CV).), and thus, the simultaneously generated pulse form signals can be identified as the signals of a light-emitting particle of one kind in the light-emitting particles contained in the sample solution while pulse form signals other than the simultaneously generated pulse form signals can be identified as signals of the other kind(s) of light-emitting particle.

As one manner, the way of detecting pulse form signals simultaneously generated in selected wavelength bands to identify a light-emitting particle in accordance with the above-mentioned present invention can be used advantageously in acquiring information of particles of two or more kinds, such as the respective existences and number density or concentration thereof. Concretely, for example, in a case of a sample solution containing particle a emitting light of wavelength I, particle b emitting light of wavelength II and particle c emitting light of wavelength I and wavelength II as illustrated in FIG. 3A, a pulse form signal appears only on the time series light intensity data of the wavelength I when the particle a passes through CV (t1); only on the time series light intensity data of the wavelength II when the particle b passes through CV (t2); and pulse form signals appear on the time series light intensity data of both the wavelength I and wavelength II when the particle c passes through CV (t3), as shown in FIG. 3B. Consequently, through detecting pulse form signals simultaneously generated on time series light intensity data of both the wavelength I and wavelength II, the particles a-c can be identified on the time series light intensity data. And by counting the numbers of the pulse form signals of particles a-c separately, it becomes possible to acquire the number density or concentration or other information thereof, repectively.

The above-mentioned way of identification of signals on time series light intensity data can be advantageously used in the detection of a binding reaction of molecules or a dissociation reaction of a molecule. For example, in a case of testing of the presence or absence and/or the degree of a binding reaction of a certain particle a and the other particle b, the particle a is labeled with a light-emitting substance (typically a fluorescent dye; the same in the following.) emitting the light of wavelength I while the particle b is labeled with a light-emitting substance emitting the light of the wavelength II. In that case, as illustrated in FIG. 3C, when the particle a or particle b by itself passes through CV (t1 or t2), a signal appears only in the wavelength I or wavelength II, respectively; but, when the particle a and particle b form a combination (a+b) and the combination passes through CV (t3), signals are generated simultaneously in both the wavelength I and wavelength II, and thus, it becomes possible to identify the binding reaction of the particle a and particle b or to estimate the degree of its strength by detecting or counting the simultaneously generated signals. As an example of a binding reaction which can be tested in such a manner, there are raised an interaction between two proteins, a hybridization of a target nucleic acid.

Moreover, in testing the presence or absence and the degree of a decomposition reaction of a certain particle, there is prepared a particle c before decomposition, to which both a label emitting the light of wavelength I and a label emitting the light of wavelength II are attached, and then, the decomposition reaction to be tested is made progress. There, if the particle c is decomposed by the decomposition reaction and thereby a particle a attached with the label emitting the light of wavelength I and a particle b attached with the label emitting the light of wavelength II are produced, then, when the particle a or b passes through CV (t1 or t2) as illustrated in FIG. 3D, a signal appears only in the wavelength I or wavelength II; but, when the non-decomposed particle c passes through CV (t3), signals are generated simultaneously in both the wavelength I and wavelength II. Thus, by comparing the frequency of the simultaneously generated signals with the frequency of the signals generated only in one of the wavelengths I and II, it becomes possible to identify the decomposition reaction of the particle c or to estimate the degree of its strength. As an example of a decomposition reaction which can be tested in such a manner, there are raised the decomposition reaction by a restriction enzyme or a polymerase which decomposes nucleic acid specifically or the decomposition reaction by a protease.

Furthermore, as an alternative manner, the way of detecting pulse form signals simultaneously generated in the selected wavelength bands and identifying a light-emitting particle according to the above-mentioned the present invention is advantageously used in a case of selecting only a signal from a particle to be observed or excluding a signal from a particle other than a particle to be observed when, as well as a light-emitting particle to be an observation object, a contaminant having the same emission wavelength as the particle to be observed is contained in a sample solution. For example, as schematically drawn in FIG. 3E, in a case of detecting a particle a emitting light of wavelength I in a sample solution, namely in a case that the particle a is a particle to be observed, if there is a contaminant x emitting the light of the wavelength I similarly and also emitting the light of the wavelength II (the contaminant x is one light-emitting particle.), a signal appears only in the wavelength I when the particle a passes through CV (t1) while signals appear in both the wavelengths I and II when the contaminant x passes through CV (t2), as illustrated in FIG. 3F. Accordingly, by identifying, as the contaminant x, the signals simultaneously generated on the time series light intensity data of the wavelengths I and II obtained in the light measurement for this sample solution, and referring to the signal generated only on the time series light intensity data of the wavelength I, it becomes possible to identify the existence of the particle a and to acquire information about the number density or concentration thereof. This manner is advantageously used, for example in a case of detecting a particle to be an observation object at low concentration in a biological material containing various contaminants such as a blood sample. Further, although not illustrated, contrarily to the above-mentioned manner, when a particle to be observed is a light-emitting particle which emits the lights of the wavelengths I and II and a contaminant emits only the light of either of the wavelengths I and II, it becomes possible to identify the existence of the particle to be observed and to acquire information about the number density or concentration thereof, by referring to only signals simultaneously generated on the time series light intensity data of the wavelengths I and II.

In this regard, although the examples of FIG. 3 show the cases where light is measured in two wavelength bands, the measurement of light may be conducted in three or more wavelength bands, and then, in the obtained time series light intensity data of the respective wavelength bands, the detection of signals simultaneously generated in the selected wavelength bands and the identification of a kind of light-emitting particle may be performed, and it should be understood that such a case belongs to the scope of the present invention.

3. Operation Processes of Scanning Molecule Counting Method

In the embodiment of the scanning molecule counting method incorporating the structure of the present invention with the optical analysis device 1 as illustrated in FIG. 1A, concretely, there are conducted (1) a process of preparation of a sample solution containing light-emitting particles, (2) a process of measuring the light intensity of a sample solution and (3) a process of analyzing the measured light intensity. FIG. 4 shows the operation processes in this embodiment in a form of flow chart.

(1) Preparation of a Sample Solution

The particle to be observed in the inventive method may be an arbitrary particle as long as it is dispersed and moving at random in a sample solution, such as a dissolved molecule, and the particle may be, for instance, a biological molecule, i.e. a protein, a peptide, a nucleic acid, a lipid, a sugar chain, an amino acid, etc. or an aggregate thereof, a virus, a cell, a metallic colloid or other non-biological molecule (Typically, the sample solution is an aqueous solution, but not limited to this, and it may be an organic solvent or other arbitrary liquids.). Also, the particle to be observed may be a particle which emits light by itself, or may be a particle to which a light emitting label (a fluorescent molecule, a phosphorescent molecule, a chemiluminescent or bioluminescent molecule) is attached in an arbitrary manner. For instance, in the testing of a binding reaction of two particles, as noted, a sample solution may be a solution which is prepared in a manner that, after attaching a light emitting label which emits light of a certain wavelength band to one of the particles and attaching the different light emitting label which emits light of the different wavelength band to the other of the particles, both of the particles are mixed appropriately and the mixture is exposed under a condition causing the binding reaction. Also, in the testing of a decomposition reaction of one particle, a sample solution may be a solution which is prepared in a manner that the particle to which different light emitting labels emitting lights of mutually different wavelength bands have been attached is exposed under a condition causing the decomposition reaction. Moreover, in detecting a certain specific particle in a solution containing a contaminant, one light-emitting label or two light-emitting labels whose emission wavelengths mutually differ will be attached to the specific particle. And, the wavelength bands to be detected may be appropriately selected based on the emission wavelength bands of the light-emitting particles in a sample. How to select a particle to be an observed object in a sample solution, how to attach light emitting label(s) to a particle to be an observation object or how to select detected wavelengths may be appropriately selected by the performer of an experiment, and it should be understood that one skilled in the art can select various combinations of particles to be observed or light emitting labels and detected wavelength bands to realize the inventive method, and any cases belong to the scope of the present invention as long as the identification of a light-emitting particle is performed according to the present invention.

(2) Measurement of the Light Intensity of a Sample Solution

The measurement of the light intensity in the optical analysis in accordance with the scanning molecule counting method of this embodiment may be performed in the same manner as the measurement process of the light intensity in FCCS, measuring the light intensities of two or more wavelength bands, except driving the mirror deflector 17 to move the position of the light detection region within the sample solution (to scan in the sample solution) during the measurement (FIG. 4—step 100). In the operation process, typically, after dispensing a sample solution into the well(s) 10 of the micro plate 9 and putting it on the stage of the microscope, when a user inputs to the computer 18 a command of a measurement start, the computer 18 executes programs (the process of changing the optical path in order to move the position of the light detection region in the sample solution, and the process of detecting light from the light detection region during the moving of the position of the light detection region) memorized in a storage device (not shown), and then illuminating the light detection region in the sample solution with the excitation light and measuring light intensity will be started. When the measurement was started, the light of the excitation wavelength of a light-emitting particle in the sample solution is emitted from the light source 2 under the control of the operation process of the computer 18 according to the programs. Especially in this embodiment, since the lights of two or more wavelength bands are detected, the wavelength(s) of the excitation light emitted from the light source 2 are selected so that the light of two or more wavelength bands to be detected will be emitted from the light-emitting particle(s). Thus, especially when the light-emitting particle emits the fluorescence of only one wavelength band with the excitation light of one wavelength band, the laser lights of two or more wavelength bands will be emitted simultaneously. On the other hand, the mirror deflector 17 drives the mirror 7 (galvanomirror) to move the position of the light detection region in the well 10 under the control of the operation process of the computer 18 according to the programs, and simultaneously with this, the photodetector 16 sequentially converts the detected light into an electric signal and transmits it to the computer 18, which generates the time series light intensity data from the transmitted signals and store it in an arbitrary manner. In this regard, in this embodiment, the respective two or more photodetectors 16 detect the lights of mutually different wavelength bands, and thereby time series light intensity data is generated for each of the detected mutually different wavelength bands. Also, the photodetector 16 is typically a super high sensitive photodetector which can detect an arrival of a single photon, and thus the detection of light may be the photon counting performed in the manner of measuring sequentially the number of photons which arrive at the photodetector for every predetermined unit time(BIN TIME), for example, every 10 μs, during a predetermined time, and accordingly the time series light intensity data will be a time series photon count data.

The moving speed of the position of the light detection region during the measurement of the light intensity may be a predetermined velocity set arbitrarily, for example, experimentally or in order to meet the purpose of an analysis. In a case of acquiring the information on the number density or concentration based on the number of detected light-emitting particles (or particles to be observed therein—the same in the following), the region size or volume through which the light detection region has passed is required, and therefore, preferably, the moving of the position of the light detection region is performed in a manner enabling the grasping of the moving distance. In this regard, because the interpretation of a measurement result will become easy if the elapsed time is proportional to the moving distance of the position of the light detection region, basically, it is preferable that the moving speed is constant, although not limited thereto.

By the way, regarding the moving speed of the position of the light detection region, in order to perform quantitatively precisely individual detection of a light-emitting particle to be observed from the measured time series light intensity data or the counting of the number of the light-emitting particles, it is preferable that the moving speed is set to a value quicker than the moving speed in the random motion, i.e., Brownian motion of a light-emitting particle. Since the light-emitting particle to be the observation object in this embodiment is a particle dispersed or dissolved in a solution and moving at random freely, its position moves with time owing to the Brownian motion. Thus, when the moving speed of the position of the light detection region is slower than the movement of a particle owing to the Brownian motion, the particle moves at random in the region as schematically drawn in FIG. 5A, whereby the light intensity changes at random (the excitation light intensity in the light detection region is reduced from the peak at the center of the region toward its outside.), so that it becomes difficult to determine a significant light intensity change corresponding to each light-emitting particle (a signal indicating light from a light-emitting particle). Then, preferably, as drawn in FIG. 5B, the moving speed of the position of the light detection region is set to be quicker than the average moving speed of a particle by the Brownian motion (diffusional moving velocity) so that the particle will cross the light detection region in an approximately straight line and thereby the profile of the change of the light intensity corresponding to each particle becomes almost uniform in the time series light intensity data as illustrated in the upper row of FIG. 5C (When a light-emitting particle passes through the light detection region in an approximately straight line, the profile of the light intensity change is similar to the excitation light intensity distribution.) and the correspondence between each light-emitting particle and light intensity can be easily determined.

Concretely, the time $\Delta t$ required for a light-emitting particle having a diffusion coefficient D to pass through the light detection region of radius Wo (confocal volume) by Brownian motion is given from the expression of the relation of mean-square displacement:

$$(2Wo)^2 = 6D \cdot \Delta t \qquad (1)$$

as:

$$\Delta t = (2Wo)^2/6D \qquad (2),$$

and thus, the velocity of the light-emitting particle moving by Brownian motion (diffusional moving velocity) Vdif, becomes approximately $$Vdif = 2Wo/\Delta t = 3D/Wo \qquad (3)$$

Then, with reference to this, the moving speed of the position of the light detection region may be set to a value sufficiently quicker than Vdif. For example, when the diffusion coefficient of a light-emitting particle is expected to be about $D=2.0\times10^{-10}$ m$^2$/s, Vdif will be $1.0\times10^{-3}$ m/s, supposing Wo is about 0.62 μm, and therefore, the moving speed of the position of the light detection region may be set to its 10 times or more, e.g. 15 mm/s. In this regard, when the diffusion coefficient of a light-emitting particle is unknown, an appropriate moving speed of the position of the light detection region may be determined by repeating the executions of a preliminary experiment with setting various moving speeds of the position of the light detection region in order to find the condition that the profile of a light intensity variation becomes an expected profile (typically, similar to the excitation light intensity distribution).

(3) Analysis of Light Intensity

When the time series light intensity data of a sample solution are obtained by the above-mentioned processes, an analysis of the light intensity as described below may be performed in the computer 18 through processes in accordance with programs memorized in a storage device.

(i) Detection of One Particle to be Observed

When the track of one particle to be observed in its passing through the light detection region is approximately straight as shown in FIG. 5B, the light intensity variation in the signal corresponding to the particle to be observed in the time series light intensity data has a bell shaped profile reflecting the light intensity distribution in the light detection region (determined by the optical system). Thus, when the time width $\Delta\pi$ for which the light intensity exceeding an appropriately set threshold value Io continues is in a predetermined range, the signal having the profile of the light intensity may be judged to correspond to one particle having passed through the light detection region, and thereby one light-emitting particle is detected. Further, when the light intensity distribution in the light detection region can be assumed as Gaussian distribution:

$$I = A \cdot \exp(-2t^2/a^2) \qquad (4),$$

and when the intensity A and the width a, computed by fitting the expression (4) to the profile of a significant light intensity (a profile which can be clearly judged not to be a background), are within the respective predetermined ranges, the profile of the light intensity may be judged to correspond to one particle having passed through the light detection region, and thereby the detection of one light-emitting particle will be done (The profile with the intensity A and the width a out of the predetermined ranges may be ignored as a noise or a contaminant in the analysis.).

(ii) The Counting of Light-Emitting Particles

As an example of operational methods, in conducting a collective detection and the counting of light-emitting particles from time series light intensity, a smoothing treatment is performed to the time series light signal data (FIG. 5C, the upper row "detected result (unsettled)") (FIG. 4—step 110, FIG. 5C mid-upper row "smoothing"). Although the light emitted by a light-emitting particle is stochastic so that gaps will be generated in data values in minute time, such gaps in the data value can be disregarded by the smoothing treatment. The smoothing treatment may be done, for example, by the moving average method (for example, Adjacent average method and Savinsky-Golay method algorithm), Percentile filter method or FFT filter method. In this regard, parameters in performing the smoothing treatment, e.g., the number of datum points in one time of the averaging, the number of times of a moving average, etc. in the moving averages method, may be appropriately set in accordance with the moving speed (scanning speed) of the position of the light detection region and/or BIN TIME in the light intensity data acquisition.

Next, on the time series light intensity data after the smoothing treatment, in order to detect a time domain (pulse existing region) in which a significant pulse form signal (referred to as "pulse signal" hereafter) exists, the first differentiation value with time of the time series light intensity data after the smoothing treatment is computed (step 120). As illustrated in FIG. 5C, the mid-low row "time differential", in the time differential value of time series light signal data, the variation of the value increases at the time of the signal value change, and thereby, the start point and the end point of a significant signal can be determined advantageously by referring to the time differential value.

After that, a significant pulse signal is detected sequentially on the time series light intensity data, and it is judged whether or not the detected pulse signal is a signal corresponding to a light-emitting particle. Concretely, first, on the time series time-differential value data of the time series light intensity data, the start point and the end point of one pulse signal are searched and determined by referring to the time differential value sequentially, so that a pulse existing region will be specified (step 130). When one pulse existing region has been specified, the fitting of a bell-shaped function is applied to the smoothed time series light intensity data in the pulse existing region (FIG. 5C, the lower row "bell-shaped function fitting"), and then, parameters of the pulse of the bell-shaped function, such as the peak intensity, Imax; the pulse width (full width at half maximum), w; the correlation coefficient in the fitting (of the least square method), etc. are computed (step 140). In this regard, although the bell-shaped function to be used in the fitting is typically Gauss type function, it may be Lorentz type function. And it is judged whether or not the computed parameters of the bell-shaped function are within the respective ranges assumed for the parameters of the bell-shaped profile drawn by a pulse signal detected when one light-emitting particle passes a light detection region, i.e., whether or not each of the peak intensity, the pulse width and the correlation coefficient of the pulse is within the corresponding predetermined range (step 150). Then, the signal, whose computed parameters of the bell-shaped function are judged to be within the ranges assumed in a light signal corresponding to one light-emitting particle, as shown in FIG. 6A left, is judged as a signal corresponding to one light-emitting particle, and thereby, one light-emitting particle has been detected, and one particle is counted (The number of particles is counted up. Step 160). On the other hand, a pulse signal, whose computed parameters of the bell-shaped function are not within the assumed ranges, as shown in FIG. 6A right, is disregarded as noise.

The search and the judgment of a pulse signal in the processes of the above-mentioned steps 130-160 are repetitively carried out in the whole region of the time series light signal data, and whenever one light-emitting particle is detected, it is counted as one particle. And, when the search of the pulse signal in the whole region of the time series light signal data is completed (step 170), the count value of particles obtained till then is considered as the number of light-emitting particles which have been detected in the time series light intensity data. Especially in this embodiment, the above-mentioned steps 110-170 may be performed in each of the time series light intensity data of the mutually different wavelength bands, and the number of the pulse signals corresponding to the light-emitting particles may be counted in each of the wavelength bands. In this regard, the process of detecting individually and counting signals of light-emitting particles from time series light intensity data may be conducted by an arbitrary way other than the above-mentioned way.

(iii) Detection and Counting of Simultaneously Generated Signals

When the detection of signals (pulse signals) corresponding to the light-emitting particles in the time series light intensity data of two or more wavelength bands is completed as noted above, signals simultaneously generated on the time series light intensity data of the selected wavelength bands are detected among the detected signals. Whether or not a signal in a certain time series light intensity data and a signal in the other time series light intensity data simultaneously appeared may be judged by whether or not the generation periods of the respective signals overlap mutually. This judgment may be conducted concretely, for example, in a manner that, when at least one of the start point tys and the end point tye of a pulse signal of the time series light intensity data of a certain wavelength band (wavelength II) are present between the start point txs and the end point txe of a pulse signal corresponding to a light-emitting particle in the time series light intensity data of another wavelength band (the first wavelength band: wavelength I), namely, when at least one of $$txs < tys < txe \tag{5a}$$

$$txs < tye < txe \tag{5b}$$

is established, it is judged that the pulse signals simultaneously generated in the wavelength I and the wavelength II have been generated. And by repeating this judgment successively on time series light intensity data, all the pulse signals simultaneously generated on the time series light intensity data of the selected wavelength bands may be detected together with the counting of their number. In this regard, in a case that there are three or more selected wavelength bands, when pulse signals whose generation periods overlap in all the selected wavelength bands exist, the pulse signals are judged as simultaneously generated signals. Further, as an alternative manner, when the difference between the time of the peak of a pulse signal in the first wavelength band and the time of the peak of a pulse signal in another wavelength band is within a predetermined time, it may be judged that those pulse signals are simultaneously generated pulse signals.

(iv) Analysis and Determination of the Number Density or Concentration of a Light-Emitting Particle The simultaneously generated signals detected as noted above and their count value are used for various analyses, depending upon the manner of an experiment. For example, in an experiment of testing a binding reaction of two particles as illustrated by FIG. 3C, simultaneously generated signals are signals from a combination of two particles, and therefore, when simultaneously generated signals are detected, this fast is the evidence of the occurrence of the binding reaction of two particles. And, since it is considered that signals other than the simultaneously generated signals are signals corresponding to the particles which have not made the binding reaction, it becomes possible to estimate the degree of the strength of the binding reaction of two particles by comparing the count value of the simultaneously generated signals with the count value of the other signals. For instance, in a case that the above-mentioned measurement of light and detection of signals are performed in various environmental conditions, a relative increase (reduction) of the count value of simultaneously generated signals under a certain condition means the increase (reduction) of the strength or the degree of the progress of the binding reaction. Further, in an experiment of testing a decomposition reaction of one particle as illustrated in FIG. 3D, it will be thought that signals other than simultaneously generated signals are generated when one particle decomposes and thereby particles having only one light emitting label are produced, and therefore, when signals other than simultaneously generated signals are detected, this fact can become an evidence of the occurrence of this decomposition reaction (see the following notes). And by comparing the count value of the simultaneously generated signals with the count value of other signals, it becomes possible to estimate the degree of the strength, the degree of the progress, etc. of the decomposition reaction. For instance, in a case that the above-mentioned measurement of light and detection of signals are performed in various environmental conditions, a relative reduction of the count value of simultaneously generated signals under a certain condition means the increase of the strength or the degree of the progress of a decomposition reaction.

[(note) However, as shown in the embodiment described later, in an actual experiment, it is difficult to coincide spatially completely CVs of the excitation lights of mutually different wavelengths, and accordingly, a region where only the excitation light of one wavelength is illuminated can be produced in the light detection region. In that case, signals which should be simultaneously generated signals if the irradiated regions of excitation light of mutually different wavelengths are coincided will be included in the signals other than the simultaneously generated signals. Namely, it is possible that, in signals other than simultaneously generated signals, the signals of the combination of two particles are included in a case of a test of a binding reaction of FIG. 3C, and the signals of particles before decomposition are included in a case of a test of a decomposition reaction of FIG. 3D. Thus, in the test of the binding reaction of FIG. 3C, the number of signals other than simultaneously generated signals itself cannot be judged as the absolute number of combinations, and in the test of the decomposition reaction of FIG. 3D, the presence or absence of a decomposition reaction cannot be judged only from an existence of a signal other than simultaneously generated signals. However, it is possible to estimate relative changes of the degree of the strength and the degree of progress of a binding reaction or a decomposition reaction by the comparison of the count value of simultaneously generated signals with the count value of the other signals.]

Furthermore, in a sample solution containing two or more kinds of light-emitting particle, in a case that a light-emitting particle corresponding to simultaneously generated signals is rendered to be a particle to be observed, an existence of a particle to be observed will be confirmed by detecting simultaneously generated signals, and since the count value of the simultaneously generated signals is considered to be proportional to the number density or concentration of the particle to be observed, it becomes possible to acquire the information about the number density or concentration of the particle to be observed by referring to the count value. Further, contrarily, in a case that simultaneously generated signals are rendered to be signals of particles other than the particle to be observed and/or contaminant, an existence of a particle to be observed is confirmed by the existence of a signal other than simultaneously generated signals, and by excluding the count value of the simultaneously generated signals from the count value of the signals on the time series light intensity data of the emission wavelength of the particle to be observed, it becomes possible to acquire the information for the number density or concentration of the particle to be observed more accurately. [As noted, in actual experiments, it is difficult to coincide spatially completely CVs of the excitation lights of mutually different wavelengths so that a region where only the excitation light of one wavelength is illuminated will be produced in the light detection region, and accordingly, an existence of a particle to be observed is not proved only from an existence of a signal other than simultaneously generated signals. However, the increase or decrease of signals other than simultaneously generated signals corresponds to increase or decrease in particles to be observed, and therefore, the increase or decrease of the particles to be observed in a sample solution can be detected from a change of the count value of signals other than simultaneously generated signals.]

The number density or concentration of a light-emitting particle in time series light intensity data can be determined using the count value of the respective light-emitting particles and the volume of the whole region which the light detection region has passed through during the acquisition of the time series light intensity data. However, the effective volume of the light detection region varies depending on the wavelength of excitation light or detected light, the numerical aperture of lenses and the adjustment condition of the optical system, and therefore, it is generally difficult to compute the effective volume of the light detection region from the design parameter values, and it is not easy to compute the whole volume which the light detection region has passed through, either. Thus, typically, the light intensity measurement, the detection of particles and the counting thereof are performed as explained above with a solution having a known light-emitting particle concentration (reference solution) under the same condition as that for the measurement of a sample solution to be tested, and then, from the detected number of light-emitting particles and the concentration of the light-emitting particle in the reference solution, the volume of the whole region which the light detection region has passed through, i.e., the relation between the detected number and the concentration of the light-emitting particle, may be determined. Preferably, the light-emitting particle of a reference solution may be a light emitting label (fluorescent dye, etc.) having the same wavelength characteristic as the corresponding light-emitting particle. Concretely, for example, supposing the detected number of the light-emitting particles is N in a reference solution of the particle concentration (number density) C, the volume Vt of the whole region which the light detection region has passed through is given by:

$$Vt = N/C \qquad (6).$$

Alternatively, the plurality of solutions of different concentrations are prepared as reference solutions and the measurement is performed for each of the solutions, and then, the average value of the computed Vt is determined as the volume Vt of the whole region which the light detection region has passed through. Thus, when Vt is given, the concentration (number density) c of the light-emitting particle of the sample solution, whose counting result of the particles is n, is given by:

$$c = n/Vt \qquad (7)$$

In this regard, the volume of the light detection region and the volume of the whole region which the light detection region has passed through may be given by an arbitrary method, for instance, using FCS and FIDA, instead of the above-mentioned method. Further, in the optical analysis device of this embodiment, there may be previously memorized in a storage apparatus of the computer 18 the information on the relations (expression (6)) between concentrations C and particle numbers N of various standard particles for assumed moving patterns of the light detection region, so that a user of the device can appropriately use the memorized information on the relation in conducting an optical analysis.

Especially in computing the number density or concentration of a light-emitting particle corresponding to simultaneously generated signals, a solution of known concentrations of light-emitting particles having emission wavelengths in all the selected wavelength bands may be prepared as a reference solution, and the detection and counting of simultaneously generated signals may be performed on time series light intensity data obtained by the measurement of the light intensity with the solution, and then, from the count value and concentration, the total volume Vt of the region through which the light detection region has passed may be determined. In calculating the concentration of each light-emitting particle in a sample solution containing two or more kinds of light-emitting particle, the count value of simultaneously generated signals may be used for the light-emitting particle corresponding to the simultaneously generated signals, and, for a light-emitting particle corresponding to signals other than the simultaneously generated signals, the value obtained by deducting the count value of the simultaneously generated signals from the count value of all the signals on the time series light intensity data of the wavelength band of the emission wavelength of the light-emitting particle.

Thus, according to the optical analysis method in which the above-mentioned inventive method is incorporated in the scanning molecule counting method, more diverse information is acquirable than the scanning molecule counting method with the light measurement of one wavelength band, and also, in conducting an optical analysis in accordance with the scanning molecule counting method for a sample solution containing light-emitting particles of two or more kinds, it becomes possible to obtain accurate results with influence of unnecessary data being reduced or eliminated. In this connection, it should be understood that, according to the scanning molecule counting method with the above-mentioned inventive method, even with a small amount of a sample solutions similarly to FCS, FCCS, FIDA, etc., diverse information can be acquired with respect to a light-emitting particle of a lower concentration (several pM level) than the level at which a good measurement is possible in the optical analysis technique including a statistical procedure in analysis processes, such as FCS, FCCS, and FIDA (typically about 1 nM).

B. Embodiment of the Invention in FCS, Etc.

In another aspect, the inventive method is used advantageously for removing a signal of light from a particle other than a particle to be observed from time series light intensity data measured in an optical analysis technique using a confocal microscope, such as FCS, FCCS, and FIDA. Concretely, in a measurement according to FCS, FCCS, FIDA, etc., in a case that a certain specific kind of light-emitting particle is rendered to be a particle to be observed and the light of the wavelength band covering the emission wavelength of the particle (it is considered as a "main measured wavelength band".) is measured to generate time series light intensity data, if there are other light-emitting particles or other contaminants (referred to as "contaminants, etc.") having an emission wavelength in a "main measured wavelength band" in a sample solution, the measurement of light and generation of time series light intensity data are conducted for a wavelength band covering the emission wavelength of "contaminants, etc." other than "the main measured wavelength band" (referred to as "sub measured wavelength band"). (The sub measured wavelength band is selected so that the emission wavelength of the particle to be observed will not be covered.). According to this structure, when a significant signal in the "sub measured wavelength band" is generated, namely, when significant signals are generated simultaneously in the main measured wavelength band and sub measured wavelength band, it is assumed that a "contaminant, etc." is present in the light detection region during the generation period of the signals. Then, by removing or deleting the data during the generation period of signals simultaneously generated in the main measured wavelength band and sub measured wavelength band from the time series light intensity data of the main measured wavelength band to be analyzed in FCS, FCCS, FIDA, etc., more accurate or improved calculation results of FCS, FCCS, FIDA, etc. will be obtained based on the time series light intensity data from which the influences of contaminants, etc. have been reduced or removed.

FIG. 7A shows in the form of a flow chart the processes in the embodiment in which the inventive method is applied to FCS, etc. as noted above. Referring to the drawing, first, the measurement of light and generation of time series light intensity data are performed in a usual manner of FCS, etc. (step 200). However, in this case, the measurement of light and generation of time series light intensity data are performed not only in the main measured wavelength, but also in the sub measured wavelength band, simultaneously (In this respect, in FCCS, usually, two kinds of particles are chosen as particles to be observed and the light measurement is performed in the emission wavelength of each particle; however, in the application of the inventive method, a wavelength band different from two emission wavelengths of the particles to be observed is optionally chosen as a sub measured wavelength band.). FIG. 7B shows an actually obtained example of the time series light intensity data of the main measured wavelength band (the upper row) and the time series light intensity data of the sub measured wavelength band (the lower row). In this example, it has been known that, by setting the main measured wavelength band to 650 nm-690 nm and the sub measured wavelength band to 565 nm-595 nm, the particle to be observed is excited by 633 nm of excitation light and detected in the main measured wavelength band while contaminants, etc. are excited by 543 nm of excitation light and detected in the main measured wavelength band and sub measured wavelength band. Then, when a contaminant, etc. enters into the light detection region, a significant signal appears in a sub measured wavelength band as shown in the drawing (Corresponding to this, the increase of light intensity (photon count) is observed also in the main measured wavelength band.), and therefore, in the generation period of the pulse form signal, it can be judged that simultaneously generated signals have appeared in the main measured wavelength band and the sub measured wavelength band. Thus, by detecting the generation of a significant pulse form signal, one by one, in the time series light intensity data of the sub measured wavelength band, simultaneously generated signals are detected (step 210), and since the generation period of those simultaneously generated signals (simultaneous generation period) is assumed to be a period during which a contaminant, etc. is present in the light detection region, it is specified as a "noise period" which should be disregarded in an analysis processing to be performed later. On the other hand, a period other than the noise period is specified as the period during which a particle to be observed is present in the light detection region, i.e., as a "signal period", (step 220). And, if possible in next analysis processing, the "noise period" will be deleted from the time series light intensity data used for the analysis processing (step 230), and using the time series light intensity data from which the noise period(s) is(are) deleted, the analytical operational processes of FCS, FCCS, FIDA, etc. (the computation of an autocorrelation function or cross correlation function or the generation of a histogram, and the fitting process) will be performed in a usual manner (step 240).

According to the above-mentioned structure, since the execution of analytical operational processes of FCS, FCCS and FIDA, etc. becomes possible while the data of the generation period of signals simultaneously generated in the main measured wavelength band and sub measured wavelength band, i.e. a period during which contaminants, etc. in a sample solution are present in the light detection region is(are) eliminated, an improvement in the accuracy of the results obtained by the analytical operation processes is expected.

In order to verify the validity of the present invention explained above, the experiments described below were conducted. In this regard, it should be understood that the following embodiments illustrate the validity of the present invention only, not intended to limit the scope of the present invention.

Embodiment 1

Experiment of Detecting Oligonucleotides Labeled with Two Differently Colored Fluorescent Dyes According to the scanning molecule counting method incorporating the inventive method, light measurements were performed in two wavelength bands with sample solutions containing an oligonucleotide labeled with two differently colored fluorescent dyes (double labeled oligonucleotide), and an oligonucleotides labeled with a single colored fluorescent dye (single labeled oligonucleotide) at various ratios, and the detection and counting of simultaneously generated signals (simultaneous generation pulses) were performed in the obtained time series light intensity data, and thereby, the range of the concentration of the double labeled oligonucleotide (the light-emitting particle corresponding to simultaneous generation pulses) which can be measured by the inventive method was verified. As a control experiment, the range of concentration of the double labeled oligonucleotide measurable by FCCS was also verified.

For the samples, there were prepared a double labeled oligonucleotide and a single labeled oligonucleotide as follows:

(Double labeled oligonucleotide)
- 488pA647: Alexa488-aaaaaaaaaaaaaaaaaaaa-Alexa647

[Oligonucleotide in which the 5' end has been modified with a fluorescent dye Alexa488, and the 3' end has been modified with a fluorescent dye Alexa647]

(Single labeled oligonucleotide)
- 488 pA: Alexa488-aaaaaaaaaaaaaaaaaaaa

[Oligonucleotide in which the 5' end has been modified with Alexa488]

- pA647: aaaaaaaaaaaaaaaaaaaa- Alexa647

[Oligonucleotide in which the 3' end has been modified with Alexa647]

The sample solutions were prepared as follows: the above-mentioned oligonucleotides each were dissolved to be at 100 µM in 10 mM Tris-HCl (pH 8.0). Subsequently, the respective solutions were diluted using a phosphoric acid buffer solution containing Tween 20 0.05% (w/w), and thereby there were prepared a solution α containing 488pA and pA647 at 10 pM, respectively, and a solution β containing 488pA647 at 10 pM. Then, the solution β and solution α were mixed at volume ratio of 100:0, 50:50, 10:90, 5:95 and 0:100 so that solutions in which the ratio of the double labeled oligonucleotide 488pA647 to the single labeled oligonucleotide (488 pA, pA647) was 100%, 50%, 10%, 5% and 0% for the respective fluorescent dyes were prepared. In this connection, when Alexa488 is excited by the excitation light of 488-nm, its fluorescence is detected in the wavelength band of 510-560-nm. On the other hand, when Alexa647 is excited by the excitation light of 633-nm, its fluorescence is detected in the wavelength band of 650-690-nm.

In the light measurement and analysis, a single molecule fluorescence measuring apparatus MF-20 (Olympus Corporation), equipped with the optical system of a confocal fluorescence microscope and a photon counting system, was used as the optical analysis device, and time series light intensity data (photon count data) were acquired for the above-mentioned respective sample solutions in accordance with the manner explained in the above-mentioned "A. (2) Measurement of the light intensity of a sample solution". In that time, a 488 nm laser light (200 µW) and a 633-nm laser light (1000 µW) were used for excitation lights, and, using band pass filters, the lights of two wavelength bands, 510 to 560 nm and 650 to 690 nm, were simultaneously and separately measured for the excitation lights of 488 nm and 633 nm, respectively, and the time series light intensity data were generated for each of the excitation light of 488 nm and excitation light of 633 nm. The moving speed of the position of the light detection region in the sample solution was set to 15 mm/second; BIN TIME was set to 10 µsec.; and for the respective sample solutions, the measurement for 2 seconds was performed 3 times, respectively. After the light intensity measurement, in accordance with the procedures described in the above-mentioned "A. (3) (ii) The counting of light-emitting particles", the smoothing treatment was applied to the time series light intensity data of each wavelength band acquired with each sample solution, and after determining the start points and the end points of pulse signals in the smoothed data, the fitting of a Gauss function to each pulse signal was carried out by the least square method, and a peak intensity, a pulse width (full width at half maximum) and a correlation coefficient (in the Gauss function) were determined. Then, only the pulse signal satisfying the following conditions:

20 µsec.<pulse width<400 µsec.

Peak intensity>1(photon/10 µsec.)

Correlation coefficient>0.95     (A)

was judged as a signal corresponding to a light-emitting particle (double labeled oligonucleotide and single labeled oligonucleotide), while a pulse signal which did not satisfy the above-mentioned conditions was disregarded as noise, and then, the number of the signals judged as a signal corresponding to a light-emitting particle was counted as "the numbers of pulses".

Subsequently, in the comparing of the pulse signals judged as corresponding to a light-emitting particle, on the data of the excitation light of 633 nm and the excitation light of 488 nm, when the difference in the time of the peak (maximum) between pulse signals was within 30 µseconds, those pulse signals were judged as a simultaneously generated pulse signal (a simultaneous generation pulse signal), and their number was counted. And, using the number of simultaneous generation pulses Nab; the number of pulses on the data of excitation light of 488 nm, Na; and the number of pulses on the data of excitation light of 633 nm, Nb; the simultaneous generation pulse signal's ratio was computed by the following expression:

(the simultaneous generation pulse signal's ratio)=$Nab/(Na+Nb-Nab)$     (8)

In FCCS as the control experiment, with the same sample solutions as the above, the fluorescence owing to the excitation light of 488 nm and the fluorescence owing to the excitation light of 633 nm were measured in a usual FCCS manner under the same conditions of excitation wavelengths and detected wavelengths as the above, respectively; the respective time series light intensity data were generated; and there were computed the autocorrelation function of the fluorescence owing to the excitation light of 488 nm, the autocorrelation function of the fluorescence owing to the excitation light of 633 nm and the cross correlation function of the fluorescence owing to the excitation light of 488 nm and the fluorescence owing to the excitation light of 633 nm; and the average particle numbers were determined by the fitting. The measurement for 20 seconds in one time was repeated 3 times for each sample solutions. Further, for the purpose of comparison with the above-mentioned simultaneous generation pulse signal's ratio, DCC (Degree of Cross Correlation), was computed by the following expression.

$DCC=nab/(na+nb-nab)$     (9)

where, nab is the average particle number computed from the cross correlation function, na is the average particle number computed from the autocorrelation function of the fluorescence owing to the excitation light of 488 nm, and nb is the average particle number computed from the autocorrelation function of the fluorescence owing to the excitation light of 633 nm.

FIG. 8 shows parts of photon count data for the excitation light of 488 nm (FIG. 8A); photon count data for the excitation light of 633 nm (FIG. 8B); data after applying the smoothing treatment to these data (FIG. 8C); and pulse signals judged as a signal of a light-emitting particle through the fitting (FIG. 8D), obtained by performing the scanning molecule counting method in accordance with the inventive method. Especially as understood with reference to FIG. 8D, simultaneously generated signals (the signals indicated with signals simultaneously generated in the drawing) were observed in the pulse signals on the data of the excitation light of 488 nm (alternate long and short dash line) and the pulse signals on the data of the excitation light of 633 nm (solid line). These simultaneously generated pulse signals are considered to be signals of the light emitted from the double labeled oligonucleotide, and therefore, it has been shown that it is possible to detect particles labeled with two differently colored fluorescent dyes with being discriminated from the others by the inventive method.

FIG. 9 are drawings of plotting the simultaneous generation pulse signal's ratios in the sample solutions containing the double labeled oligonucleotide mixed at various ratios, computed by the processes of the scanning molecule counting method in accordance with the inventive method (FIG. 9A) and DCC in the sample solutions containing the double labeled oligonucleotide mixed at various ratios, computed in accordance with FCCS (FIG. 9B) against the ratio of the double labeled oligonucleotide in the sample solutions (the mixed double labeled oligo percentage), respectively. Referring to these drawings, in the results obtained by the scanning molecule counting method of the inventive method (A), the simultaneous generation pulse signal's ratio was proportional to the mixed double labeled oligo percentage in the entire tested region, where the dispersion in three measurements was very small also. Since the double labeled oligonucleotide concentration is 10 pM when the mixed double labeled oligo percentage=100%, and the concentration of the double labeled oligonucleotide is 0.5 pM when the mixed double labeled oligo percentage=5%, the results of FIG. 9A suggests that, according to the present invention, a double labeled light-emitting particle at about 0.5 pM can be detected and its concentration can also be determined. (See (note) below). On the other hand, in the result (FIG. 9B) of FCCS, when the mixed double label oligo percentage is less than 50%, the proportionality relation between the mixed double label oligo percentage and DCC was lost, and the dispersion was also large.

Thus, it has been shown that, according to the present invention, the detection of a double labeled light-emitting particle and the determination of its concentration can be achieved in the concentration range significantly lower than the range determinable by FCCS ((Namely, it is shown that, in a case that the simultaneous generation pulse signal is identified as a particle to be observed and the other signals are identified as particles other than the particle to be observed, the particle to be observed can be detected and its concentration can be determined in the concentration range lower than ever.). Further, the above-mentioned results show that, according to the present invention, in a test of an interaction (a binding reaction or a decomposition reaction) of two or more kinds of light-emitting particle, the detection of the presence or absence of the interaction of light-emitting particles and/or estimation of the degree of its strength are possible even in a case that the concentrations of light-emitting particles in a sample solution are significantly lower than the range usable in FCCS, or in a case that the interaction is weak so that combinations or decomposition products can be produced at only a relatively small amount with which their detection is difficult in FCCS.

[(note) In an actual experiment, due to the chromatic aberration in the optical system of a confocal microscope, it is usually difficult to coincide completely the regions (CV) illuminated by the excitation lights of two or more wavelengths. Thus, in the light detection region, region(s) where only the light of either one wavelength among two or more wavelengths is illuminated is generated, and therefore, when a double labeled light-emitting particle enters into such a region, signals will not be generated simultaneously on time series light intensity data of the two or more wavelength bands. So, as seen in FIG. 9A, the simultaneous generation pulse signal's ratio can be smaller than the value expected theoretically form the ratio of double labeled light-emitting particles in the sample solution. However, as understood from the drawing, the relation between the amount of double labeled light-emitting particles and the amount of the simultaneous generation pulse signals is proportional or the one to one relation, and therefore, it becomes possible to estimate the increase or decrease or concentration of the double labeled light-emitting particles in the sample solution based on the amount of the simultaneous generation pulse signals.]

Embodiment 2

Detection of Concentration of a Particle to be Observed in a Sample Solution Containing a Contaminant It has been verified that, in detecting the concentration of a particle to be observed in a sample solution containing a contaminant having the same emission wavelength as the particle to be observed by a scanning molecule counting method, the inventive method improves its accuracy.

For the samples, fluorescent dye TAMRA was used as a particle to be observed, and fluorescent dye ATTO590, a model of a contaminant. When TAMRA is excited by the excitation light of 543-nm, its fluorescence will be detected in the wavelength band of 565-595-nm. Also, when ATTO590 is excited by excitation light of 543-nm, fluorescence will be detected in the wavelength band of 565-595 nm and the wavelength band of 650-690-nm. Further, for sample solutions, there were prepared solutions containing ATTO590 at 100 pM and TAMRA at 0 pM, 1 pM, and 10 pM in a phosphate buffer including 0.05% Tween20. Also, for control solutions, there were prepared solutions containing TAMRA at 0 pM, 1 pM, and 10 pM without ATTO590.

The light measurement and analysis were performed, using the above-mentioned sample solutions, respectively, similarly to Embodiment 1 with the excitation light being a 543-nm laser light (500 µW) and the detected wavelength bands being set to 565-595 nm and 650-690 nm, and the number of pulse signals corresponding to the light-emitting particle on the time series light intensity data of each detected wavelength band and the number of simultaneous generation pulse signals were obtained. In this regard, in the detection of simultaneously generated pulse signals, when the time between the peaks of pulse signals was within 100 µseconds, the set of the pulse signals was judged as a simultaneous generation pulse signal.

FIG. 10 is a drawing in which the numbers of pulses obtained with each sample solution in accordance with the above-mentioned processes is plotted against the concentrations of TAMRA in the sample solutions. With reference to the drawing, the number of pulses (Δ) of the sample solution containing no ATTO590 was almost proportional to the concentration in the entire observed concentration range, and the high linearity of the approximate line in accordance with least-squares method was obtained (the y-intercept=0.27, the mean square error $R^2$=0.9998). In contrast, in the number of pulses (O) of the sample solution containing ATTO590, no proportional relation against the concentration was observed in the low concentration range, and the linearity of the approximate line according to a least-squares method was low (the y-intercept=30.92, the mean square error $R^2$=0.9898). However, the value (□) obtained by deducting the number of simultaneous generation pulse signals from the number of pulses of the sample solution containing ATTO590 was almost proportional to the concentration in the entire observed concentration range, and the linearity of the approximate line in accordance with the least-squares method was improved compared with the case of the sample solution containing ATTO590 (the y-intercept=10.80, the mean square error $R^2$=0.9997). In this case, the simultaneously generated pulse signals are considered to be the light from ATTO590, the model of the contaminant. Thus, the above-mentioned results show that, by eliminating the simultaneously generated pulse signals corresponding to ATTO590 from the pulse signals of the sample solution containing ATTO590, the proportional relation between the concentration of TAMRA of the particle to be observed and the pulse signals can be improved. Namely, the above-mentioned results suggest that, in a case of detecting a particle to be observed in a sample solution containing a contaminant and measuring the concentration of the particle to be observed by the scanning molecule counting method, the accuracies in detection of the particle to be observed and measurement of its concentration can be improved by identifying simultaneous generation pulse signals as signals of a particle other than the observation object and eliminating those simultaneous generation pulse signals from data in accordance with the inventive method.

Embodiment 3

Measurement of a Particle to be Observed in a Sample Solution Containing a Contaminant by FCS It has been verified that, in conducting an optical analysis in FCS for a particle to be observed in a sample solution containing a contaminant having the same emission wavelength as the particle to be observed, the accuracy of the analysis result is improved by the inventive method.

For the samples, fluorescent dye ATTO633 was used as a particle to be observed, and DNA (plasmid pbr322, Takara Bio, Inc., Cat. No. 3035) fluorescently labeled with fluorescent dye SYTOX Orange (Invitrogen Corp., Cat. No. S-11368) (fluorescently labeled DNA) was used as a model of a contaminant. When ATTO633 is excited by the excitation light of 633-nm, its fluorescence is detected in the wavelength band of 650-690-nm. And, when SYTOX Orange bound with DNA is excited by the excitation light of 543-nm, its fluorescence is detected in the wavelength band of 565-595 nm and the wavelength band of 650-690-nm. For the sample solution, there was prepared a solution containing 100 pM ATTO633, 1 pM DNA and 9 nM SYTOX Orange in an aqueous solution containing 10 mMTris-HCl (pH 8.0) (In preparing the solution, the mixed SYTOX Orange and DNA was incubated at the room temperature for 30 minutes so that SYTOX Orange could be fully combined with DNA.). In addition, for a control solution, a solution containing 100 pM ATTO633 without fluorescently labeled DNA was prepared.

For the light measurement and analysis, a single molecule fluorescence measuring apparatus MF-20 (Olympus, Inc.) was used as an optical analysis device. In the light measurement, 543 nm laser light (300 μW) and 633-nm laser light (100 μW) were used for the excitation lights, and using band pass filters, the light intensities of two wavelength bands of 565 to 595 nm and 650 to 690 nm, were simultaneously and separately measured for the excitation lights of 543 nm and 633 nm, respectively, and thereby, the time series light intensity data of each of the excitation light of 543 nm and the excitation light of 633 nm was generated. The measurement for 20 seconds was performed 2 times for each sample solution. In this case, since the fluorescence of ATTO633, the particle to be observed, is detected in the wavelength band of 650-690-nm, the detected wavelength of 650-690 nm is the main measured wavelength bands, and the detected wavelength of 565-595 nm is the sub measured wavelength band. In the analysis of the time series light intensity data, the autocorrelation function of the time series light intensity data of the main measured wavelength band (the detected wavelength of 650 to 690 nm) was calculated in the usual manner of FCS, and the following expression:

[Expression 1]

$$C(\tau) = 1 + \frac{1}{N}\left(1 + \frac{\tau}{\tau_D}\right)^{-1}\left(1 + \frac{\tau}{AR^2\tau_D}\right)^{-1/2} \quad (10)$$

(where τ is a correlation time; N is an average particle number in CV; AR is a structure parameter (the ratio of the long axis wz and the lateral radius wo of CV, (AR=wz/wo)); and τD is a translational diffusion time.) was fit to the autocorrelation function, and thereby the average particle number N and translational diffusion time τD were determined. In this connection, as described in "Embodiment of the Invention in FCS, etc.", in removing signals simultaneously generated in both the main measured wavelength band and sub measured wavelength band corresponding to a contaminant (fluorescently labeled DNA) etc., prior to the above-mentioned operation and fitting of the autocorrelation function, a time in which the photon count value exceeded beyond two photons was detected in the sub measured wavelength band, and the period for 50 μseconds before or after the detected time was identified as a "noise period". Then, as depicted in FIG. 11A, the data of the period corresponding to the "noise period" was deleted in the main measured wavelength band, and data continuous in time was reconstructed by connecting the data of the "signal period"s before and after the deleted period, and the above-mentioned operation and fitting of the autocorrelation function were conducted.

FIGS. 11B and 11C show the average particle number and the translational diffusion time (with DNA) in the case that the calculation and fitting of the autocorrelation function were performed without deletion of "noise period" as described above in the time series light intensity data of the above-mentioned sample solution (solution containing ATTO633 and fluorescently labeled DNA), the average particle number and the translational diffusion time (simultaneous generation signals, deleted) in the case that the calculation and fitting of the autocorrelation function were performed after deletion of "noise period" as described above in the time series light intensity data of the above-mentioned sample solution; and the average particle number and the translational diffusion time of the control solution (solution of ATTO633 without DNA) (without DNA), respectively. As understood from the drawings, although the average particle number and the translational diffusion time of the sample solution, computed without deleting the "noise period", each were larger than the average particle number and the translational diffusion time of the control solution, the average particle number and the translational diffusion time of the sample solution computed with deletion of the "noise period"

became closer to the values of the control solution, respectively. These results show that by identifying a generation period of simultaneously generated signals as a "noise period" and excluding it in an analytical operation of FCS, etc. in accordance with the above-mentioned inventive method, contribution of the light from light-emitting particles other than the particle to be observed is eliminated or reduced, and the accuracy in the result of the analytical operation is improved.

Thus, as understood from the results of the above-mentioned embodiments, according to the above-mentioned inventive method, by measuring the lights of two or more wavelength bands and detecting simultaneously generated signals individually in the measured time series light intensity data of two or more wavelength bands, the detection of the light-emitting particle of a specific kind included in a sample solution and the determination of its concentration becomes possible. Further, according to the present invention, by classifying signals depending upon whether or not pulse form signals generated in time series light intensity data have been simultaneously generated in two or more wavelength bands, a kind of light-emitting particle in a sample solution can be identified. Moreover, by making signals simultaneously generated in two or more wavelength bands correspond to a particle to be observed or another light-emitting particle, and selecting or excluding the simultaneously generated signals, the influences of the light from light-emitting particles other than the particle to be observed are reduced in the detection of the particle to be observed; the detection of its concentration and other arbitrary analysis, and thereby, improvements of the accuracy in the measurement results or analytical results are expected. In this connection, it should be understood that, in the inventive method, since signals simultaneously generated in two or more wavelength bands are individually detected, even when the number density or concentration in a sample solution of a light-emitting particle corresponding to the signals simultaneously generated in two or more wavelength bands is low, it is possible to "pick up" pulse signals simultaneously generated in two or more wavelength bands from the time series light intensity data, and therefore, an optical analysis becomes possible for a light-emitting particle at a low concentration of the level unobservable in an optical analysis technique using statistical procedures, such as FCS and FCCS. Usually, in optical analysis techniques, such as FCS and FCCS, the concentration of the particles to be an observation object should be about 1 nM; however, as in the above-mentioned embodiments, according to the present invention, a light-emitting particle at several pM can be to be a particle to be observed, and also, in an arbitrary light measurement and an analytical experiment, it is possible to eliminate from the measured and analytical results or reduce the influences of the light of several pM of light-emitting particles other than the particle to be observed.

In addition, in accordance with the inventive method, the light measurement may be performed in three or more wavelength bands while signals simultaneously generated in at least two wavelength bands among the wavelength bands are detected, and the analyses (the counting of particles, determination of the concentration or number density, etc.) similar to the above may be conducted for simultaneously generated signals and the other signals, detected therein, respectively, and it should be understood that such a case belongs to the scope of the present invention, also.

The invention claimed is:

1. A method of detecting and analyzing light from a sample solution containing light-emitting particles of two or more kinds moving at random using an optical system of a confocal microscope or a multiphoton microscope, the method comprising steps of:
    measuring intensities of lights of two or more wavelength bands from a light detection region of the optical system in the sample solution simultaneously and by the wavelength band to generate a time series light intensity data individually for each of the wavelength bands; and
    detecting signals indicating light from a light-emitting particle and simultaneously generated on the time series light intensity data of at least two wavelength bands among the two or more time series light intensity data, and
    identifying the simultaneously generated signals as signals of a light-emitting particle of at least one specific kind among the two or more kinds of light-emitting particle.

2. The method of claim 1, wherein when a generation period of a signal indicating light of a light-emitting particle in a time series light intensity data of a first wavelength band among the two or more wavelength bands overlaps a generation period of a signal indicating light of a light-emitting particle in a time series light intensity data of at least one wavelength band other than the first wavelength band among the two or more wavelength bands, the signal in the time series light intensity data of the first wavelength band and the signal in the time series light intensity data of the at least one wavelength band other than the first wavelength band are detected as the simultaneously generated signals.

3. The method of claim 1, further comprising a step of detecting individually each signal indicating light from a light-emitting particle in each of the time series light intensity data, and identifying a kind of each light-emitting particle which emitted light indicated by the corresponding signal based upon whether or not the signals have been simultaneously generated in at least two selected wavelength bands among the two or more wavelength bands.

4. The method of claim 3, identifying signals simultaneously generated in the at least two selected wavelength bands as signals of a particle to be observed among the light-emitting particles of the two or more kinds; and identifying a signal indicating light from a light-emitting particle other than the simultaneously generated signals as a signal of a light-emitting particle other than the particle to be observed.

5. The method of claim 4, in which the two or more wavelength bands are two wavelength bands, the method identifying signals simultaneously generated on the time series light intensity data of the two wavelength bands as the signal of the particle to be observed, and identifying a signal indicating light from the light-emitting particle generated only on one of the time series light intensity data of the two wavelengths as a signal of a light-emitting particle other than the particle to be observed.

6. The method of claim 3, identifying signals simultaneously generated in at least two selected wavelength bands as signal of a light-emitting particle other than a particle to be observed among the light-emitting particles of the two or more kinds; and identifying a signal indicating light from a light-emitting particle other than the simultaneously generated signals as a signal of the particle to be observed.

7. The method of claim 6, in which the two or more wavelength bands are two wavelength bands, the method identifying signals simultaneously generated on the time series light intensity data of the two wavelength bands as a signal of a light-emitting particle other than the particle to be observed, and identifying a signal indicating light from a light-emitting particle generated only on one of the time series light intensity data of the two wavelength bands as a signal of the particle to be observed.

8. The method of claim 3, in which the measuring of the intensities of the lights of two or more wavelength bands from the light detection region is performed with moving a position of the light detection region of the optical system in the sample solution by changing an optical path of the optical system; and each signal indicating light from a single light-emitting particle is detected individually in each of the time series light intensity data.

9. The method of claim 8, further comprising a step of counting a number of the individually detected signals indicating light from the single light-emitting particles.

10. The method of claim 8, wherein the position of the light detection region is moved at a predetermined speed.

11. The method of claim 8, wherein the position of the light detection region is moved at a velocity quicker than a diffusional moving velocity of the light-emitting particle in the sample solution.

12. The method of claim 11, further comprising a step of determining a number density or a concentration of the light-emitting particle based on a number of the signals indicating light from the light-emitting particle in the sample solution.

13. The method of claim 1, identifying signals simultaneously generated in at least two selected wavelength bands among the two or more wavelength bands as signals of a light-emitting particle other than a particle to be observed among the light-emitting particles of the two or more kinds.

14. The method of claim 13, removing, from the time series light intensity data, data of a generation period of the signal identified as the signal of light-emitting particles other than the particle to be observed.

15. The method of claim 14, performing an optical analysis by fluorescence correlation spectroscopy, fluorescence intensity distribution analysis method, or fluorescence cross correlation spectroscopy, using the time series light intensity data that shows the light intensity from the particle to be observed among the time series light intensity data of the two or more wavelength bands.

* * * * *

```
                         SEQUENCE LISTING

<160> NUMBER OF SEQ ID NOS: 1

<210> SEQ ID NO 1
<211> LENGTH: 20
<212> TYPE: DNA
<213> ORGANISM: Artificial
<220> FEATURE:
<223> OTHER INFORMATION: used for a test of a scanning moleclue counting
      method

<400> SEQUENCE: 1
aaaaaaaaaa aaaaaaaaaa                                                       20
```